United States Patent [19]
Yoshida

[11] Patent Number: 6,018,391
[45] Date of Patent: Jan. 25, 2000

[54] METHOD AND APPARATUS FOR INSPECTING FOREIGN MATTER BY EXAMINING FREQUENCY DIFFERENCES BETWEEN PROBING LIGHT BEAM AND REFERENCE LIGHT BEAM

[75] Inventor: Haruo Yoshida, Gyoda, Japan

[73] Assignee: Advantest Corporation, Tokyo, Japan

[21] Appl. No.: 09/014,624

[22] Filed: Jan. 28, 1998

[30] Foreign Application Priority Data

Jan. 28, 1997 [JP] Japan ..................................... 9-014175

[51] Int. Cl.[7] ........................................................ G01B 9/02
[52] U.S. Cl. ......................... 356/349; 356/351; 356/237.4
[58] Field of Search .................................. 356/349, 345, 356/359, 360, 237.3, 237.4, 351; 250/559.41

[56] References Cited

U.S. PATENT DOCUMENTS

| | | | |
|---|---|---|---|
| 4,842,408 | 6/1989 | Yoshii et al. ............................ | 356/349 |
| 5,343,290 | 8/1994 | Batchelder et al. .................... | 356/349 |
| 5,486,919 | 1/1996 | Tsuji et al. .............................. | 356/349 |
| 5,591,985 | 1/1997 | Tsuji et al. ......................... | 250/559.41 |

*Primary Examiner*—Samuel A. Turner
*Attorney, Agent, or Firm*—Staas & Halsey LLP

[57] ABSTRACT

A light beam from a light source is divided by a beam splitter into two branches, thereby providing a probing light having a single linear polarization and a reference light having a linear polarization which has the same polarization axis as that of the probing light. A frequency shifter which is driven in accordance with a modulation signal shifts the frequency of at least one of the probing light and the reference light. The probing light irradiates a specimen to be inspected, and the light reflected from the specimen and the reference light impinge on a photoelectric transducer to be heterodyned to provide a beat signal. A parameter representing the nature of a foreign matter is extracted from the beat signal and the reference signal used as the modulation signal, and the extracted parameter is processed to detect the presence of a foreign matter.

47 Claims, 10 Drawing Sheets

FIG. 18

| | FIG.12 (PRIOR ART) | | FIG.13 (INVENTION) | |
|---|---|---|---|---|
| | PROBING LIGHT | REFERENCE LIGHT | PROBING LIGHT | REFERENCE LIGHT |
| (1) | PBS  FS  BS<br>$1\times(0.7\times0.5)\times0.7\times0.8$<br>$=0.196$ | $1\times(0.7\times0.5)\times0.7\times0.8$<br>$=0.196$ | BS           FS<br>$1\times(0.8\times0.97)\times(0.7)$<br>PF<br>$\times(0.7\times0.5)=0.19012$ | |
| (2) | PBS<br>$0.196\times(0.7\times0.5)$<br>$=0.0686$ | | | |
| (3) | | PBS<br>$0.196\times(0.7\times0.5)$<br>$=0.0686$ | p→s reflect<br>$0.19012\times((1-0.1)\times0.05)$<br>$=8.5554\times10^{-3}$ | BS          FS<br>$1\times(0.8\times0.03)\times(0.7)$<br>PF<br>$\times(0.7\times0.5)=8.400\times10^{-3}$ |
| (4) | p→s reflect<br>$0.0686\times(0.1\times0.05)$<br>$=3.43\times10^{-4}$ | $0.0686\times0.05$<br>$=3.43\times10^{-3}$ | BS<br>$8.5554\times10^{-3}\times(0.8)$<br>$=6.84\times10^{-3}$ | BS<br>$8.400\times10^{-3}\times(0.8)$<br>$=6.72\times10^{-3}$ |

METHOD AND APPARATUS FOR INSPECTING FOREIGN MATTER BY EXAMINING FREQUENCY DIFFERENCES BETWEEN PROBING LIGHT BEAM AND REFERENCE LIGHT BEAM

FIELD OF THE INVENTION

The invention relates to a method of detecting particles by heterodyne detection using polarized light and an apparatus for carrying out the same, and in particular, to such a method and an apparatus which are employed to detect the presence of microscopic particles which may cause a reduction in the yield during the manufacturing steps of semiconductor devices of highly integrated circuits by applying a heterodyne detection of polarizations and an associated analysis.

BACKGROUND OF THE RELATED ART

Microscopic foreign matters or particles which cause a reduction in the yield during the manufacture of semiconductor devices of highly integrated circuits comprise metals, organic or inorganic materials or mixtures thereof, which are birefringent materials in a broad sense when considered optically. When a linearly polarized wave impinges upon a birefringent material, the wave is converted into a linearly polarized wave having a polarization plane which is orthogonal to that of the incident linearly polarized wave for part or all of the power of either transmitted or reflected wave, and is generally changed into an elliptically polarized wave. Obviously, the polarization of the transmitted or reflected wave changes depending on the angle formed between the polarization plane of the incident linearly polarized wave and the optical axis of the birefringent material. By irradiating such a microscoptic foreign matter with polarized light and analyzing light which comes from the foreign matter as a result of reflection, refraction or birefringence, it is possible to detect the presence of such a microscopic foreign matter. A technique which employs the irradiation of foreign matter with polarized light to detect the presence of foreign matter is already implemented in practical use, allowing microscopic foreign matter or defect which has been hardly detectable in the prior art to be detected with a high S/N ratio, as disclosed in Japanese Laid-Open Patent Application No. 6-317534, for example, which will be briefly summarized below.

Referring to FIG. 1, a laser beam radiated from a laser source 1 is passed through a polarizer 2 and a polarized beam splitter 5 to be separated into a pair of s-polarization and p-polarization which are linearly polarized in mutually orthogonal directions. Frequencies of these polarized light beams are modulated in accordance with mutually different shift frequencies $\omega$ and $(\omega+\Delta\omega)$ in frequency shifters 9, 11, respectively,. The modulated polarized light beams are combined together in a polarization beam splitter 12 to produce a single laser beam 12a having a pair of linear polarizations in mutually orthogonal directions which have a relative shift frequency $\Delta\omega$ therebetween. The combined beam is then separated by a polarization beam splitter 15 into a p-polarization 15a and an s-polarization 15b, which are then reflected by reflecting mirrors 18, 19, respectively, so as to irradiate a common spot 20 to be inspected on the surface of a specimen 21 disposed on a movable stage 22 from two distinct directions.

In a region of the surface of the specimen 21 which is free from foreign matter, p-polarized light which is reflected by the mirror 18 to impinge on the surface of the specimen is reflected to be incident on a polarizer 27. The incident p-polarized light is cut off if the polarization axis of the polarizer 27 is chosen to be at right angles to the p-polarization. On the other hand, in the same region, s-polarized light from the mirror 19 is reflected by the surface of the specimen and cannot impinge on the polarizer 27 which is located on the side as the mirror 19 with respect to a plane passing through the spot 20 and that is perpendicular to a plane containing the points of reflections on the mirrors 18, 19 and the spot 20. Accordingly, there is no output from a photoelectric transducer 29 for the region which is free from microscopic foreign matter. However, when microscopic foreign matter or defect which is present on the surface of the specimen is irradiated at spot 20 by rays of p- and s-polarizations from the mirrors 18 and 19, there is an incidence on the polarizer 27 of 0-order diffracted light (reflected light) 23 having s-polarization which is changed from the p-polarization and scattered light 25 having the s-polarization. It will be seen that polarization components of diffracted light 23 and scattered light 25 in the direction of the polarization axis of the polarizer 27 (that is, $\omega$ modulation component and $(\omega+\Delta)$ modulation component) pass through the polarizer 27 to be incident on the transducer 29. In this manner, a difference frequency component between diffracted light and scattered light, which will be hereafter referred to as "beat signal", is optically heterodyned or detected by the transducer 29 while the irradiated spot 20 is scanned across the foreign matter. A beat signal processing unit 30 is connected to the output of the transducer 29 and determines the width of the beat signal, thus calculating the size of the foreign matter. The polarization is only subject to a change due to the presence of foreign matter or defect, and only that light which has its linear polarization influenced by the presence of foreign matter or defect passes through the polarizer 27 to be incident as an interference input on the transducer 29 to produce the beat signal. Accordingly, a foreign matter or defect to be detected which is located on a surface to be inspected can be detected and/or inspected with a high S/N ratio while discriminating it from any other pattern other than foreign matter or defect such as a circuit pattern or the like. However, this technique only enables the detection of the intensity of the beat signal obtained by the optical heterodyne detection, but information concerning the nature of the foreign matter cannot be obtained.

The apparatus for inspecting microscopic foreign matter as described is arranged to cause the pair of p- and s-polarizations which are linear polarizations in mutually orthogonal directions to irradiate the common spot 20 to be inspected which is located on the surface of the specimen and which has a diameter on the order of 0.3 $\mu$m in two distinct directions. It is to be noted that an adjustment of the reflecting mirrors 18, 19 to bring the irradiating spots of the p- and s-polarizations into coincidence with each other on the surface of the specimen and an alignment of the optical axes of the p-and s-polarizations relative to each other are not a simple matter to implement. The described apparatus may be used in combination with a separate analyzer such as EPMA (Electron Probe Micro-Analyzer) which uses an electron beam, and in such instance, because the apparatus used for inspection of foreign matter requires that the reflecting mirrors 18, 19 be disposed on the opposite sides of the plane extended from the beam splitter 15, it is possible that this restricts or removes the freedom of disposing elements of the analyzer which is to be combined with the apparatus.

In the described apparatus, the laser beam is separated into the pair of linear polarizations in orthogonal directions or p- and s-polarizations, one of which is used as probing light to be used for detection while the other is used as reference light, and thus the powers of the both are at the proportion of 1:1. The probing light is scattered by foreign matter or defect present on the surface of the specimen while being changed in polarization, but the proportion of the scattered light is as low as several percents. Thus, the luminous energy of the detection signal is low, as is the signal intensity. To increase the luminous energy of the detection signal, it is necessary to construct an optical system which provides a greater proportion of luminous energy for the probing light.

SUMMARY OF THE INVENTION

It is an object of the invention to provide a method of inspecting foreign matter by a heterodyne detection of polarizations which permits information concerning the nature of a foreign matter detected to be obtained, and which is simplified in construction and provides a better detection efficiency to overcome the described problems of the prior art, and an apparatus for carrying out the method.

The method for detecting foreign matter by using polarized light heterodyne detection according to the invention comprises the steps of:

(a) producing probing light having a linear polarization and a reference light which includes at least the same polarization component as the linear polarization from a light beam emitted from light source means;

(b) shifting the frequency of at least one of the reference light and the probing light so as to provide a frequency offset therebetween and producing a reference signal having the offset frequency;

(c) using the probing light to which the frequency offset is provided to irradiate a specimen to be inspected and providing a relative movement between an irradiating spot of the probing light and the specimen;

(d) causing reflected light form the specimen and the reference light which is shifted in frequency relative to the probing light to impinge on photoelectric transducer means to cause an optical heterodyne detection of the frequency offset to be detected as a beat signal;

(e) extracting a parameter representing the nature of a foreign matter present on the specimen from the beat signal and the reference signal; and (f) deriving information concerning the nature of the foreign matter by analysis of the extracted parameter.

The apparatus for detecting foreign matter by using polarized light heterodyne detection according to the invention comprises:

light source means for emitting a coherent light beam;

beam splitter means for producing probing light including a linear polarization and reference light which includes at least the same polarization component as the linear polarization from a light beam emitted from the light source means;

frequency modulation means for frequency modulating at least one of the reference light and the probing light to provide a frequency offset therebetween and producing a reference signal having the offset frequency;

scan means for using the probing light to which the frequency offset is given to irradiate a specimen to be inspected and providing a relative movement between an irradiating spot of the probing light and the specimen;

photoelectric transducer means on which the probing light reflected from the specimen and the reference light which is modulated relative to the probing light impinge to be optically heterodyned thereon to provide the frequency offset, which is detected as a beat signal;

means for extracting a parameter representing the nature of a foreign matter present on the specimen from the beat signal and the reference signal; and means for analyzing the extracted parameter to derive information concerning the nature of the foreign matter.

BRIEF DESCRIPTION OF THE DRAWINGS

FIG. 18 is a chart showing a comparison of luminous energy at selected points in the apparatus shown FIGS. 16 and 17.

DETAILED DESCRIPTION OF THE PREFERRED EMBODIMENTS

Several embodiments of the invention will now be described with reference to the drawings.

Figure 2:
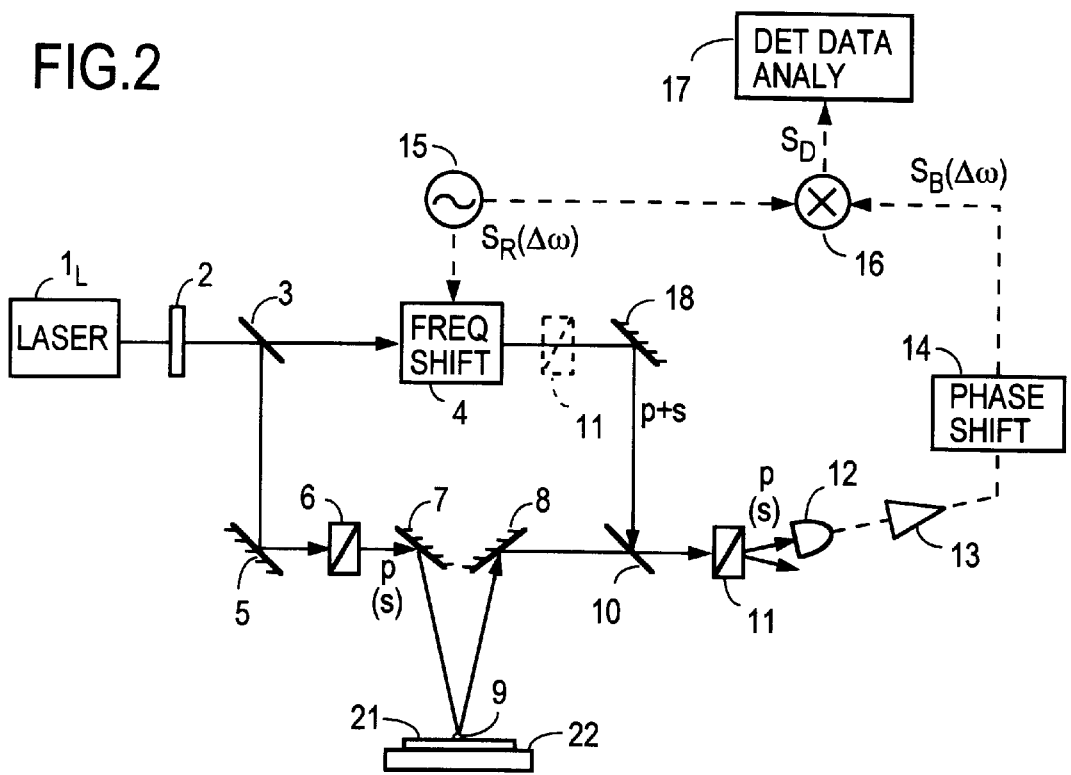
FIG. 2 is a schematic view of a first embodiment of the invention.

Referring to FIG. 2 for describing a first embodiment of the invention, a laser source $1_L$ which oscillates in a single mode emits a coherent light beam, which passes through a rejection filter 2 which eliminates unnecessary modes. The coherent beam then impinges upon a beam splitter 3 which has no dependency on polarization to be divided into two branches. The light beam in one of the branches, which travels downward as viewed in FIG. 2, is referred to as probing light while the other light beam which travel straightforward is referred to as reference light.

The reference light has not yet undergone any separation in respect of polarization, but contains the same polarization component as the probing light. The reference light is modulated in a frequency shifter 4 which is driven by a reference signal $S_R(\Delta\omega)$ from an electrical oscillator 15 which oscillates at frequency of $\Delta\omega$, and obtains a different wavelength or a frequency offset of $\Delta\omega$ from the probing light. Subsequently, the reference light is reflected by a reflecting mirror 18 to be incident on a beam splitter 10.

On the other hand, after being reflected by a reflecting mirror 5, the probing light impinges upon a polarization filter 6 which selects either p-wave or s-wave of the linear polarization. It is assumed here that the selected probing light represents p-wave. A reflecting mirror 7 then reflects p-wave probing light to irradiate a specimen 21. Light which irradiates and is reflected from the specimen 21 provides an optical detection signal, which is reflected by a reflecting mirror 8 to be incident on the beam splitter 10. In order to detect the presence of a microscopic foreign matter 9 on the surface of the specimen 21, a polygon mirror may be used for the reflecting mirror 7 to scan the light beam or an stage 22 on which the specimen 21 is disposed may be arranged to be movable.

The optical detection signal which is incident on the beam splitter 10 is synthesized with the reference light which has not yet undergone any separation in respect of polarization, and the synthesized light beam impinges on a Wollaston prism or any other polarization separating filter 11 where only p-polarization component which is the same as the probing light is selected. The p-polarization component of the reference light and p-polarization of the probing light are optically heterodyned on the light receiving surface of a photoelectric transducer 12 to provide a signal difference frequency therebetween or a beat signal $S_B(\Delta\omega)$). Of importance to the present invention is an extraction of a parameter such as a differential amplitude, a differential phase or a differential vector from the reference signal $S_R(\Delta\omega)$ and the beat signal $S_B(\Delta\omega)$ by utilizing a mixer, a phase detector or a vector detector in a parameter extractor 16, thus permitting the amplitude difference, the phase difference or the vector difference of the beat signal $S_B(\Delta\omega)$ with respect to the reference signal $S_R(\Delta\omega)$ to be obtained. The difference signal varies depending on the nature of the foreign matter, and accordingly, by obtaining such differential signals, it is possible to obtain information not only relating to the size of the foreign matter, but also relating to the nature of the foreign matter.

An amplifier 13 and a phase shifter 14 are used to adjust the amplitude and the phase of the beat signal $S_B(\Delta\omega)$ so that an output level from a parameter extractor 16 is zero when a microscopic foreign matter is absent or so that the beat signal is equal to the modulation signal (or reference signal) $S_R(\Delta\omega)$ which drives the frequency shifter 4. Consequently when the probing light irradiates a microscopic foreign matter 9, its polarization is influenced, and the power of the p-polarization component of the probing light which passes through the polarization separating filter 11 will be greatly reduced as is the amplitude of the beat signal which is output from the photoelectronic transducer 12. As a result, the mixer 16 delivers the reference signal $S_R(\Delta\omega)$ substantially in its entirety. The beat signal $S_B(\Delta\omega)$ and the reference signal $S_R(\Delta\omega)$ from the oscillator 15 which is used as a modulation signal in the frequency shifter 4 are electrically heterodyned in the extractor 16, for example, and the probing light which irradiates the surface of the specimen 21 is relatively swept by a rotation of the reflecting mirror 7 or a movement of the stage 22, thereby providing a final detection signal $S_D$ as a difference signal which is an output from the mixer 16. A detection data analyzer 17 calculates the size, the configuration or any other characteristic of the microscopic foreign matter on the basis of the final beat signal $S_D$.

Figure 3:
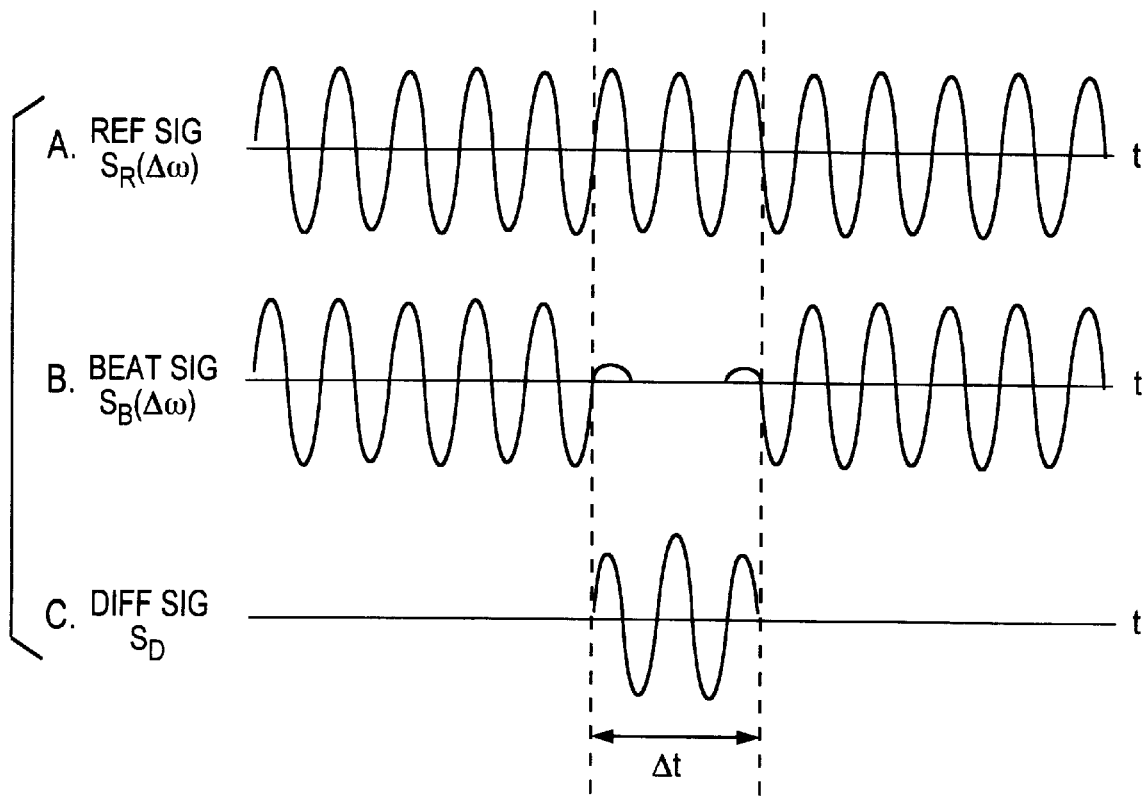
FIG. 3 is a series of waveform diagrams of a reference signal, a beat signal and difference signal shown in FIG. 2.

Referring to FIG. 3, a waveform A represents the reference signal $S_R(\Delta\omega)$ which is produced by the oscillator 15 and which is used as a modulation signal in the frequency shifter 4. A waveform B represents a beat signal as the irradiated beam spot of the probing light moves across the microscopic foreign matter 9 being inspected as a result of a movement of the stage 22 or the sweep of the probing light. In this example, the fact that the microscopic foreign matter 9 which is a birefringent material located on the surface of the specimen is irradiated by the probing light, whereby the polarization has changed during a time interval $\Delta t$, for example, from p-polarization to s-polarization, is indicated by a reduced amplitude of the beat signal $S_B(\Delta\omega)$. When the microscopic foreign matter, or a birefringent material on the surface of the specimen, is not irradiated by the probing light, namely, other than the time interval $\Delta t$, the beat signal $S_B(\Delta\omega)$ which is applied to the parameter extractor 16 has the same frequency, amplitude and phase as the waveform A. A result of heterodyning, for example, the waveforms A and B together results in a difference signal, which is indicated by a waveform C. It is to be noted that the envelope of the difference waveform substantially represents the profile of the microscopic foreign matter which is traversed by the light beam. The time duration $\Delta t$ of the waveform C on the time axis which is divided by the relative speed of movement of the probing light with respect to the stage 22 represents a size of the microscopic foreign matter which is traversed by the light beam. If no microscopic foreign matter is present, and accordingly as long as the waveforms A and B are waveforms exhibiting the same frequency, amplitude and phase, an output obtained as a result of mixing the waveforms A and B together is equal to zero.

It is to be noted that as indicated in broken lines in FIG. 2, instead of disposing the polarization separating filter 11 between the synthesizing beam splitter 10 and the photoelectric transducer 12, the filter 11 may be disposed in the optical path of the reference light between the beam splitter 3 and the synthesizing beam splitter. In this instance, the probing light which has its polarization changed, for example, from p-polarization to s-polarization, by the presence of a foreign matter impinges upon the photoelectric transducer 12, producing no interference or heterodyned detection with the reference light or p-polarization, and is detected as a d.c. component, which is not desirable.

In the described apparatus for inspecting foreign matter by a heterodyned detection of polarizations, the probing light is synthesized with the reference light subsequent to the reflection at the specimen 21 to be subject to an optical heterodyne detection on the light receiving surface of the photoelectric transducer 12. Accordingly, when the proportion of luminous energy to each branch which is determined by the beam splitter 3 is chosen such that the luminous energy of the both is substantiously equal to each other on the light receiving surface, the signal-to-noise ratio (S/N) of the signal detection can be improved. In the embodiment of FIG. 2, the frequency shifter 4 is disposed in the optical path of the reference light, namely, in the optical path extending from the beam splitter 3 through the reflecting mirror 18 to the beam splitter 10, but it will be apparent that it may be disposed in the optical path for the probing light, namely, in the optical path extending from the beam splitter 3 through the reflecting mirrors 5, 7, the specimen 21 and the reflecting mirror 8 to the beam splitter 10.

As described, the first embodiment utilizes only one polarization component for the optical probing operation, and a difference signal for a desired parameter is obtained from the beat signal $S_B(\Delta\omega)$ available from a result of the optical probing and the reference signal $S_R(\Delta\omega)$ and is subject to an electrical data processing to derive information concerning the foreign matter.

Figure 4:
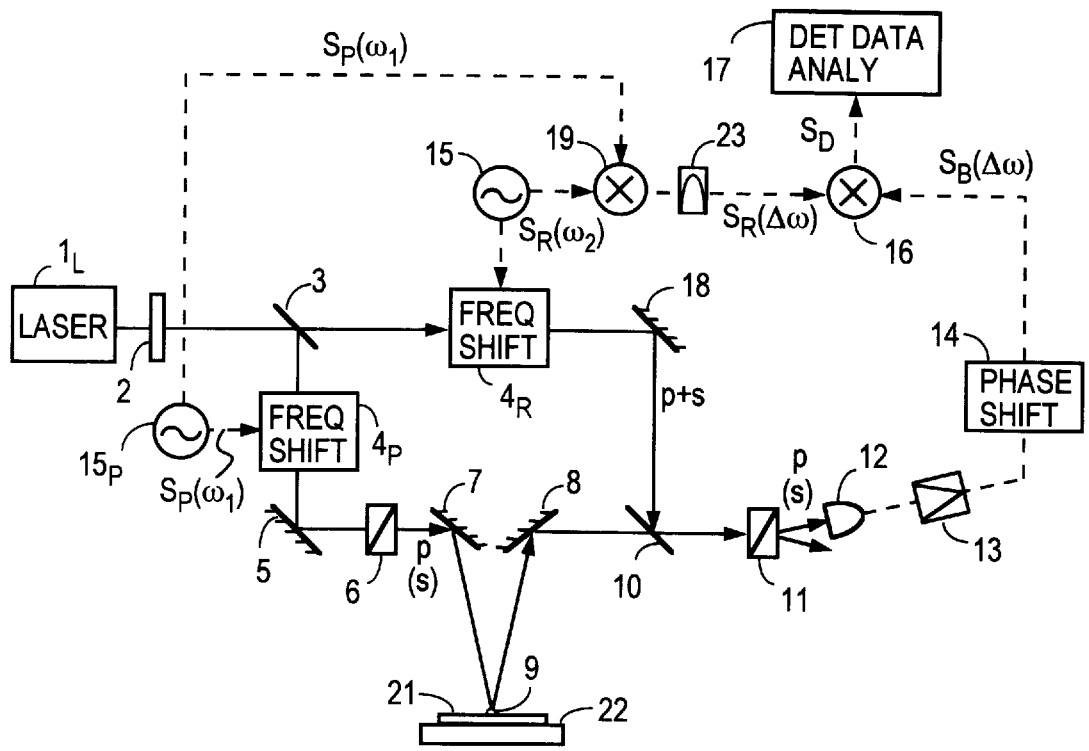
FIG. 4 is a schematic view of a second embodiment of the invention.

Referring to FIG. 4, a second embodiment of the invention will be described. It is to be noted that parts appearing in FIG. 4 which correspond to those shown in FIG. 2 are designated by like difference numerals and characters as used in FIG. 2. A laser source $1_L$ which oscillates in a single mode emits a coherent light beam which is passed through a rejection filter 2 which eliminates unnecessary modes. The light beam is then incident on a beam splitter 3 having no dependency upon the polarization to be divided into two branches, the light beam in one branch which travels downward as viewed in FIG. 4 is referred to as probing light while the other light beam which travels straightforward is referred to as reference light.

The reference light which travels straightforward has not yet undergone any separation in respect of polarization, but contains the same polarization component as the probing light. The reference light is modulated in a frequency shifter $4_R$ which is driven in accordance with a signal $S_R(\Delta\omega)$ from an electrical oscillator $15_R$ which oscillates at a frequency of $\omega_2$, and thus obtains a different wavelength from the probing light and hence a frequency offset of $\omega_2$. Subsequently, the reference light is reflected by a reflecting mirror 18 to be incident on a beam splitter 10.

On the other hand, the probing light is modulated in a probing light frequency shifter $4_P$ which is driven by a signal $S_P(\omega_1)$ from a second oscillator $15_P$ which oscillates at a frequency of $\omega_1$, and is then on incident a reflecting mirror 5, which reflects it to pass through a polarization filter 6, which is operative to select either linear polarization, namely, p-wave or s-wave. It is assumed here that the probing light selected by the polarization filter 6 represents p-polarization. The p-polarization probing light is reflected by a reflecting mirror 7 to irradiate a microscopic foreign matter 9. The reflected light which is obtained as a result of irradiation of the foreign matter 9 provides an optical detection signal, which is reflected by a reflecting mirror 8 to be incident on the beam splitter 10. To scan a specimen 21 with the probing light beam, a polygon mirror may be used for the reflecting mirror 7 or a stage 22 on which the specimen 21 is disposed may be moved to effect a relative scan with the light beam.

Upon incidence on the beam splitter 10, the optical detection signal is again synthesized with the reference light which has not yet undergone any separation in respect of polarization, and the synthesized light beam is incident on Wollaston prism or any other polarization separation filter 11, which selects only the same polarization component, which is p-polarization in the present example. The synthesized light beam is then optically heterodyned on the light receiving surface of a photoelectric transducer 12 to be converted into an electronic signal, which is a beat signal $S_B(\Delta\omega)$ having a frequency of $\Delta\omega=|\omega_1-\omega_2|$.

A narrow bandwidth amplifier 13 and a phase shifter 14 are used to adjust the amplitude and the phase of the beat signal $S_B(\Delta\omega)$ so that it is equal to an output signal from a mixer 19 (or a reference signal), which represents a difference frequency signal $S_R(\Delta\omega)$ between modulation signal $S_P(\omega_1)$ and $S_R(\omega_2)$ which drive the phase shifters $4_P$ and $4_R$, respectively, when no microscopic foreign matter 9 is present. In the second embodiment, the amplifier which corresponds to the amplifier 13 of the first embodiment is formed by the narrow bandwidth amplifier 13, which is introduced in order to eliminate 1/f noises of the photoelectric transducer 12, and is effective to set the frequency $\Delta\omega$ of the beat signal $S_B(\Delta\omega)$ or the difference frequency signal between the modulation signals $\omega_1$ and $\omega_2$ which is obtained by an optical heterodyne detection on the light receiving surface of the photoelectric transducer 12 higher than a frequency, which is commonly referred to as a corner frequency where the 1/f noise level of the photoelectric transducer 12 and white noise level are substantially equal to each other, bringing the center frequency of the narrow bandwidth amplifier 13 into coincidence with such beat frequency. A first oscillator $15_P$ oscillates at a signal frequency $\omega_1$ and a second oscillator $15_R$ oscillates at a signal frequency $\omega_2$, and the both signal frequencies are mixed in the second mixer 19, and a bandpass filter 23 selects a difference frequency $\Delta\omega=|\omega_1-\omega_2|$, which is chosen as a reference signal $S_R(\Delta\omega)$.

The beat signal $S_B(\Delta\omega)$ and the reference signal $S_R(\Delta\omega)$ having the difference frequency $\Delta\omega=|\omega_1-\omega_2|$ which is extracted from the second mixer 19 by the bandpass filter 23 are electrically heterodyned in a parameter extractor 16, an output of which provides the difference signal $S_D$ as a final detection signal. A detection data analyzer 17 calculates the size, shape or any other characteristic of a microscopic foreign matter on the basis of the final detection signal $S_D$.

Figure 5:
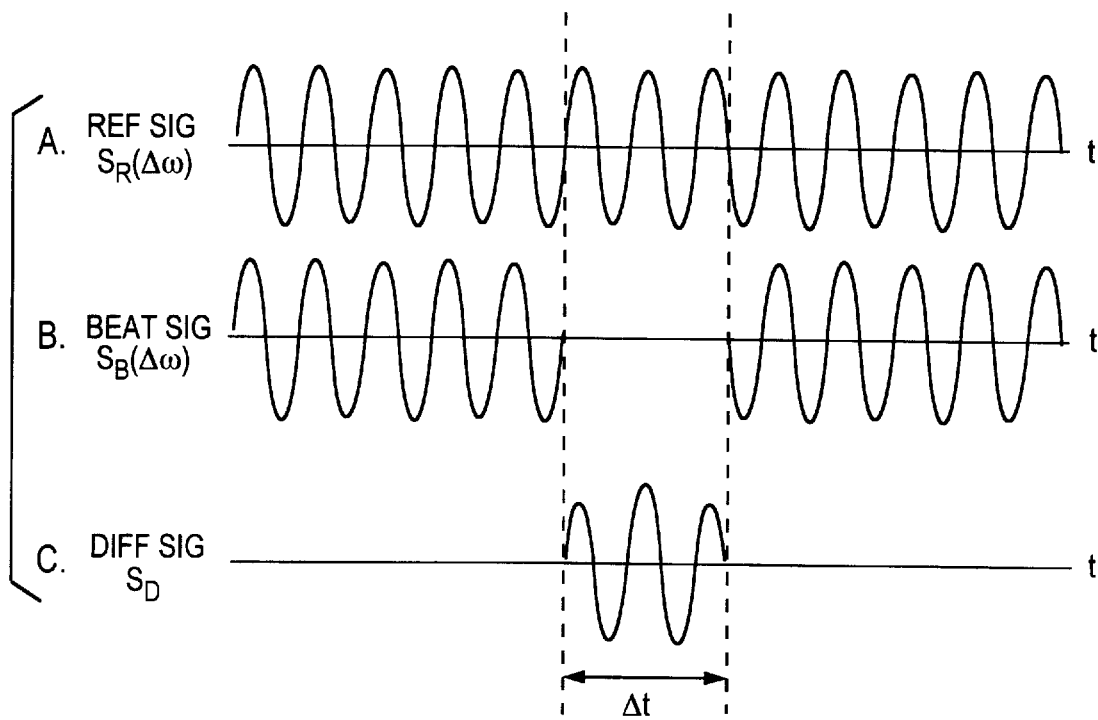
FIG. 5 is a series of waveform diagrams of a reference signal, beat signal and a difference signal shown in FIG. 4.

Referring to FIG. 5, a waveform A represents a signal waveform having the difference frequency $\Delta\omega=|\omega_1-\omega_2|$ which is obtained as a result of mixing the signal $S_P(\omega_1)$ which has the signal frequency $\omega 1$ from the first oscillator $15_P$ and the signal $S_R(\omega_2)$ having the signal frequency $\omega_2$ from the oscillator $15_R$ in the second mixer 21 or the reference signal $S_R(\Delta\omega)$. A waveform B represents a waveform of the beat signal $S_B(\Delta\omega)$ as the probing light traverses across a microscopic foreign matter which comprises a birefringent material through a sweep of the probing light or a movement of a stage 22. FIG. 5 shows that the microscopic foreign matter is irradiated over a time interval $\Delta t$ and p-polarization component is substantially changed into a different polarization, for example, into s-polarization and this is detected by a reduction in the amplitude. It is to be noted that when a region other than the microscopic foreign matter is being irradiated by the probing light, the waveform B has a waveform having the same frequency, amplitude and phase as the waveform A. A waveform C represents a difference signal waveform which is obtained as a result of mixing the waveforms A and B. The interval $\Delta t$ during which the difference signal waveform appears substantially represents a length of a microscopic foreign matter which is traversed by the probing light. The duration $\Delta t$ of the waveform C on the time axis which is divided by the relative speed of movement of the foreign matter or the probing light represents a size of the microscopic foreign matter. In region where no microscopic foreign matter is present and the both waveforms A and B exhibits the same frequency, amplitude and phase, an output obtained as a result of mixing the waveforms A and B is equal to zero.

The probing light which comprises a single polarization component is synthesized with the reference light, subsequent to the detection of an object being inspected, and is optically heterodyned on the light receiving surface of the photoelectric transducer 12 also in the second embodiment, and accordingly, if the proportioning of the luminous energy by the beam splitter 3 is chosen so that the luminous energy of each signal on the light receiving surface is substantially equal to each other, the signal-to-noise ratio (SIN) during the signal detection can be improved. Again, the polarization separating splitter 11 may be disposed in the optical path of the reference light between the beam splitter 3 and the synthesizing beam splitter 10.

Figure 6:
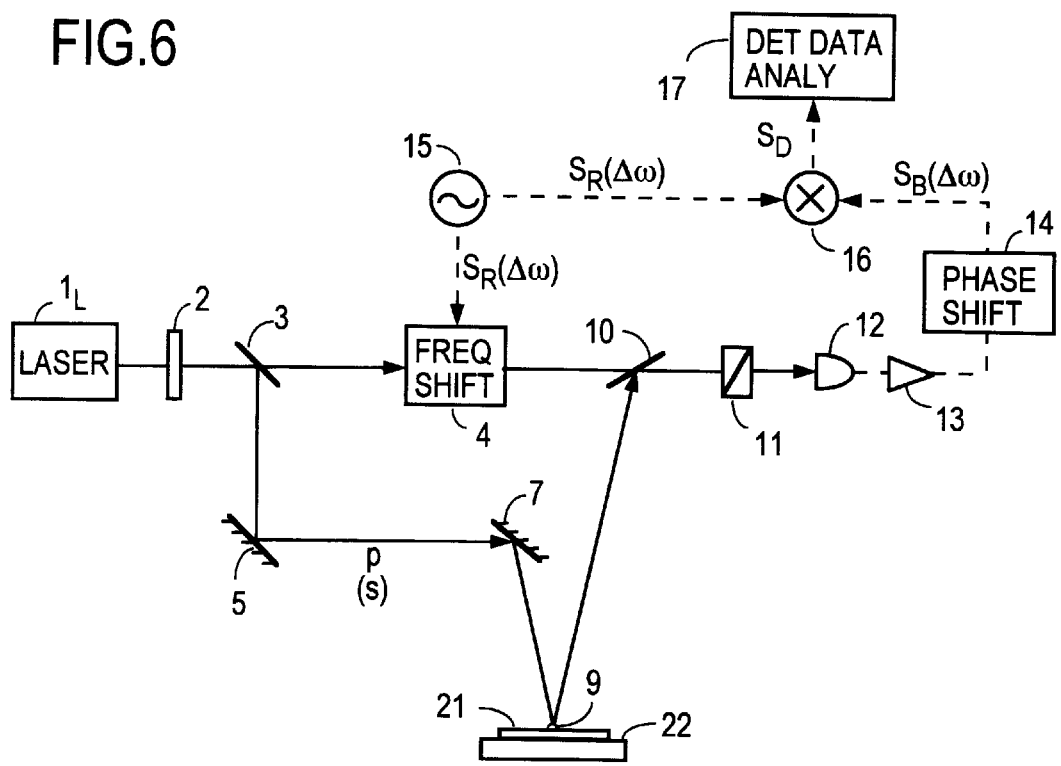
FIG. 6 is a schematic view of a third embodiment of the invention.

Referring to FIG. 6, a third embodiment of the invention will be described. In the third embodiment, the reflecting mirrors 8 and 18 shown in the first embodiment of FIG. 2 are omitted, and a beam splitter 10 is used to synthesize light from a frequency shifter 4 and light from a specimen 21 to be inspected. Obviously, a polarization separating filter 11 may be disposed in the optical path between a beam splitter 10 and a photoelectric transducer 12 as mentioned previously in connection with the embodiment shown in FIG. 2.

A laser source $1_L$ oscillates in a single mode and emits a coherent light beam, which is fed through a rejection filter 2 which eliminates unnecessary modes. The coherent light is then incident on a beam splitter 3 having no dependency upon polarization to be divided into two branches. A light beam in one of the branches, or that travelling downward as viewed in FIG. 6, is referred to as probing light while the other light beam which travels straightforward is referred to as reference light.

The reference light is modulated in a frequency shifter 4 which is driven by an oscillation signal from an oscillator 15, whereby it has a different optical wavelength from or has a frequency offset $\Delta\omega$ from the probing light. Subsequently, the reference light is incident on a polarization separating filter 11, which selects the same polarization as in the probing light, and is then incident on a beam splitter 10.

On the other hand, the probing light is reflected by a reflecting mirror 5 to be incident on a polarization filter 6, which is operative to select a linear polarization, for example, p-wave for transmission. The p-wave probing light is reflected by a reflecting mirror 7 to irradiate the surface of a specimen 21 to be inspected. Reflected wave which is reflected from the specimen 21 provide an optical detection signal, which is incident on the beam splitter 10.

The optical detection signal which is incident on the beam splitter 10 is then again synthesized with the reference light which has the same polarization plane with the optical detection signal, but having a frequency offset of $\Delta\omega$, and the synthesized wave is optically heterodyned on the light receiving surface of a photoelectric transducer 12 to provide a beat signal $S_B(\Delta\omega)$.

An amplifier 13 and a phase shifter 14 are used to adjust the amplitude and the phase of the beat signal $S_B(\Delta\omega)$ so that it is equal to a modulation signal $S_R(\Delta\omega)$ which drives the frequency shifter 4 in the absence of a microscopic foreign matter 9. The beat signal $S_B(\Delta\omega)$ and the reference signal $S_R(\Delta\omega)$ from the oscillator 15, which is also used as a modulation signal applied to the frequency shifter 4, are electrically heterodyned, for example, in a parameter extractor 16, an output of which provides a difference signal as a final detection signal $S_D$. A detection data analyzer 17 calculates a size, a shape or any other characteristic of the microscopic foreign matter on the basis of the final detection signal $S_D$.

In this manner, the further embodiment shown in FIG. 6 operates on the similar principle of operation as the first embodiment shown in FIG. 2, and respective waveforms of the reference signal $S_R(\Delta\omega)$, the beat signal $S_B(\Delta\omega)$ and the difference signal $S_D$ are completely the same as the waveforms A, B and C as shown in FIG. 3.

Figure 7:
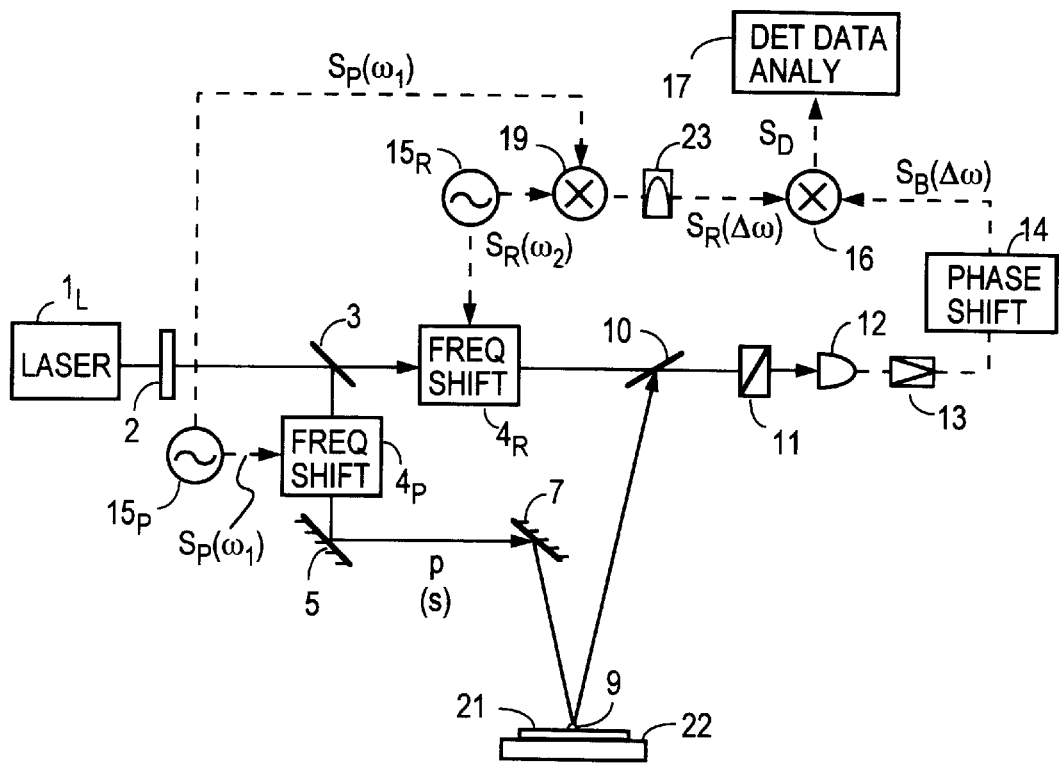
FIG. 7 is a schematic view of a fourth embodiment of the invention.

FIG. 7 shows a fourth embodiment of the invention. In this embodiment, the reflecting mirrors 8 and 18 in the second embodiment shown in FIG. 4 are omitted, as in the third embodiment shown in FIG. 6, and a beam splitter 10 is arranged to synthesize light from a frequency shifter 4 and light from a specimen 21 to be inspected. In addition, a polarization separating filter 11 is disposed in an optical path between the frequency shifter 4 and the beam splitter 10, selecting the same polarization component of the reference light as the polarization component of the probing light before the wave synthesis takes place. Accordingly, the principle of operation of this embodiment remains the same as in the embodiment shown in FIG. 4, and therefore will not be described. Similarly, waveforms of a reference signal $S_R(\Delta\omega)$, an electrical detection signal $S_B(\Delta\omega)$ and a difference signal $S_D$ in FIG. 7 correspond to signal waveforms A, B and C shown in FIG. 5.

In each of the embodiments shown in FIGS. 2, 4, 6 and 7, the laser source $1_L$ has been described as emitting laser light containing both p- and s-polarization components. However, alternatively, the laser source $1_L$ may be of a construction to emit either one of p- and s-polarization, or a linear polarizing filter may be provided on the output side of the laser source $1_L$ for selectively transmitting only p- or s-polarization to be applied to a measuring optical system. The application of such an arrangement to the embodiments shown in FIGS. 6 and 7 are illustrated in FIGS. 8 and 9, respectively.

Figure 8:
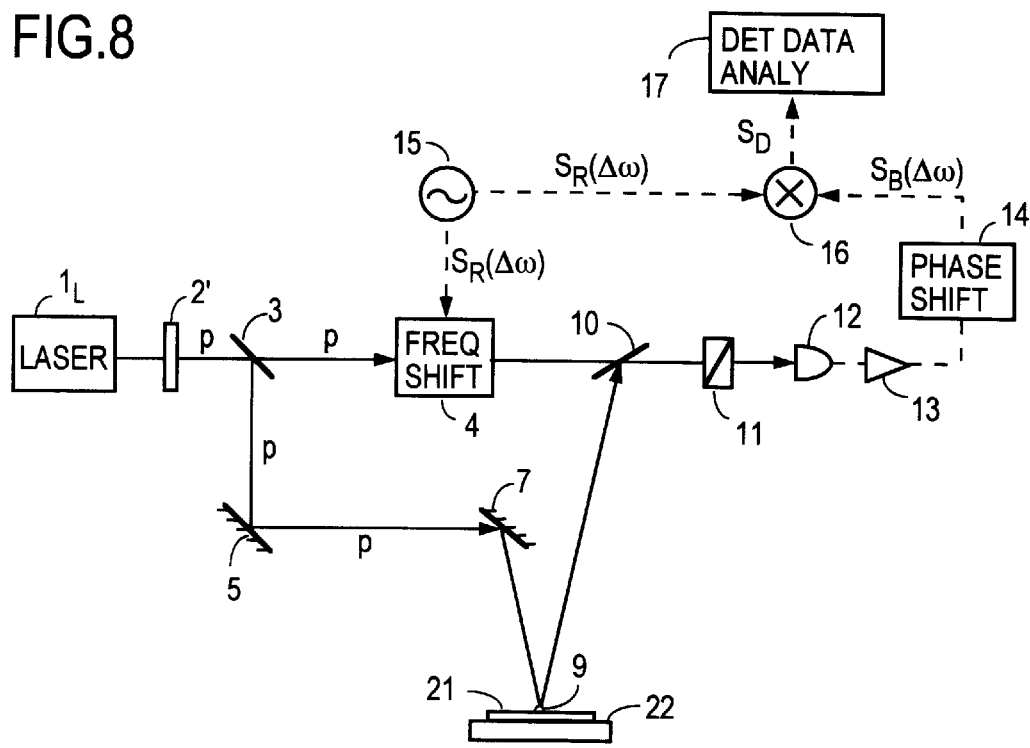
FIG. 8 is a schematic view showing a modification of FIG. 6.

In the embodiment shown in FIG. 8, linear polarizing filter 2' is disposed on the output side of a laser source $1_L$, which may transmit only p-polarization, for example, to be fed to a beam splitter 3. The beam splitter 3 has no dependency upon polarization, and divides the incident p-polarization into two branches each representing a probing light beam and a reference light beam to be fed to a reflecting mirror 5 and a frequency shifter 4, respectively. Since the probing light already represents p-polarization, the polarization filter 6 of the embodiment shown in FIG. 6 is unnecessary and is accordingly dispensed with. In other respects, the arrangement is similar to the arrangement shown in FIG. 6. In this embodiment, when a laser source which delivers only p-polarization, for example, is used as the laser source $1_L$, the polarization filter 2' can also be dispensed with.

Figure 9:
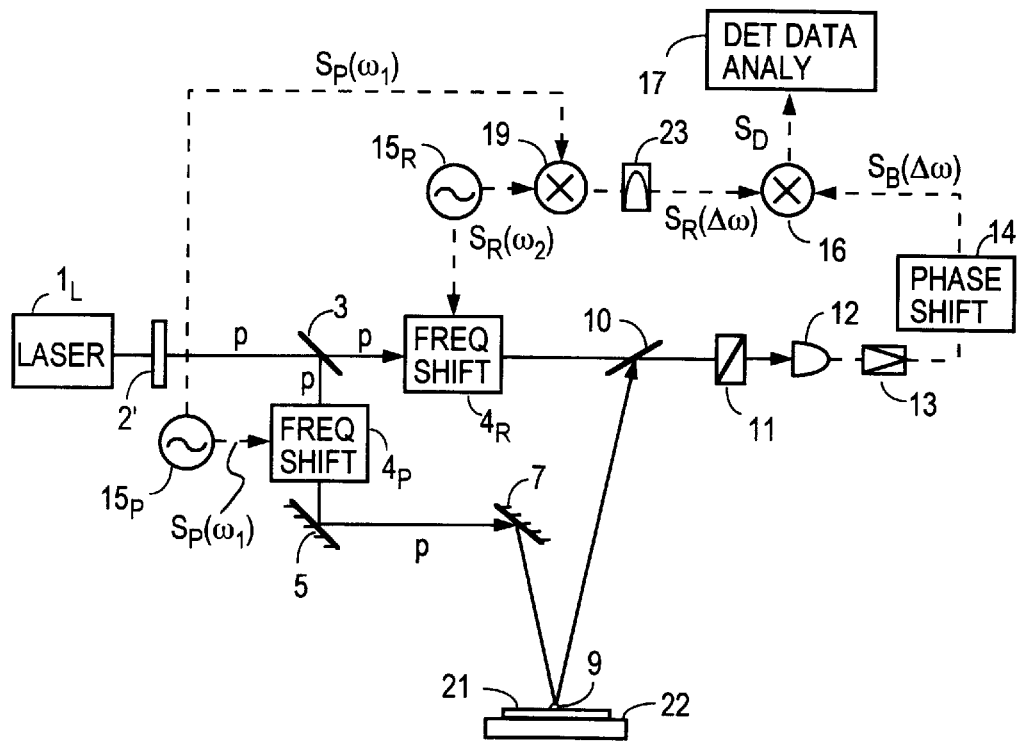
FIG. 9 is a schematic view showing a modification of FIG. 7.

In the embodiment shown in FIG. 9, a polarization filter 2' is also provided on the output side of a laser source $1_L$ similarly, which may selectively transmit only p-polarization, for example, and a beam splitter 3 having no dependency upon polarization divides an output light into two branches each representing a reference light beam and a probing light beam, respectively. It will be noted that the polarization filter 6 shown in FIG. 7 is not used. In other respects, the arrangement is similar to that shown in FIG. 7.

As mentioned previously, it is the principle of the invention that the probing light comprising only either p- or s-polarization from a light source is used to irradiate a specimen 21 to be inspected and the probing light is optically heterodyned by a photoelectric transducer 12 against the same polarization component of the reference light from the same light source as contained in the probing light, but which has a frequency offset relative to the probing light, thus providing a beat signal, and a difference signal for a desired parameter is derived from the beat signal and the reference signal. Accordingly, in each of the embodiments mentioned above, the beam splitter 3 having no dependency upon polarization is used to divide the laser light from the light source into the branches so that both the probing light beam and the reference light beam contains the same linearly polarized component. However, the principle of the invention can be carried out by using a different technique, which is illustrated in FIGS. 10 and 11 as modifications of the embodiments shown in FIGS. 6 and 7, respectively.

Figure 10:
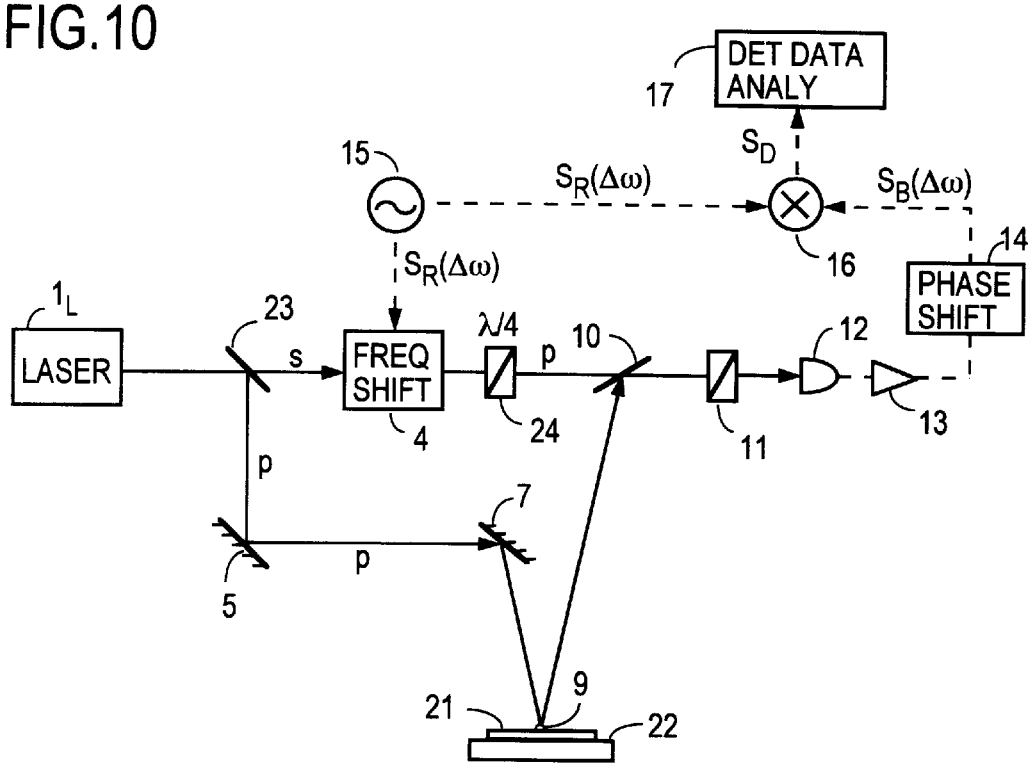
FIG. 10 is a schematic view illustrating a further modification applied to FIG. 6 or 8.

The modification shown in FIG. 10 is illustrated in a manner corresponding to the arrangement of FIG. 6, and it will be noted that in this modification, the beam splitter 3 having no dependency upon polarization which is shown in FIG. 6 is replaced by a polarized beam splitter 23, which is effective to separate the laser light from the laser source $1_L$ into p- and s-polarization, which are used as probing light and reference light, respectively. Accordingly, the polarization filter 6 shown in FIG. 6 is omitted. As an alternative, p-polarization may be used as the reference light while s-polarization may be used as probing light. Describing the modification in terms of the example shown in FIG. 10, the probing light having the p-polarization is caused to irradiate a specimen 21 to be inspected by a suitable arrangement of reflecting mirrors 5 and 7 while the reference light having s-polarization is fed to a frequency shifter 4.

What is characterizing the modification is the disposition of a quarter-wave plate 24 in the optical path of the reference light between the polarization separating prism 23 and the synthesizing beam splitter 10, thus converting s-polarization into p-polarization. In the example shown, the quarter-wave plate 24 is disposed in the optical path between the frequency shifter 4 and the synthesizing beam splitter 10, and the reference beam which is converted into p-polarization by the quarter-wave plate 24 is synthesized with the probing light reflected from the specimen 21 in the synthesizing beam splitter 10. The synthesized beam is fed to a photoelectric transducer 12 through a polarization filter 11 having its polarization axis coincident with p-polarization. In other respects, the arrangement is similar to that of FIG. 6. Accordingly, an interference between the probing light and the reference light which has the same polarization as the probing light on the light receiving surface of the photoelectric transducer 12 is enabled, and thus an optical heterodyned detection is enabled in this modification in the similar manner as in the previous embodiments. It should be understood that there is no interference between p-and s-polarization. In this embodiment, since the full power of the p-polarization component from the light source $1_L$ can be used for the probing light which irradiates the specimen 21, there is obtained an advantage that the efficiency of use of the laser light from the light source is improved over the described embodiments.

Figure 11:
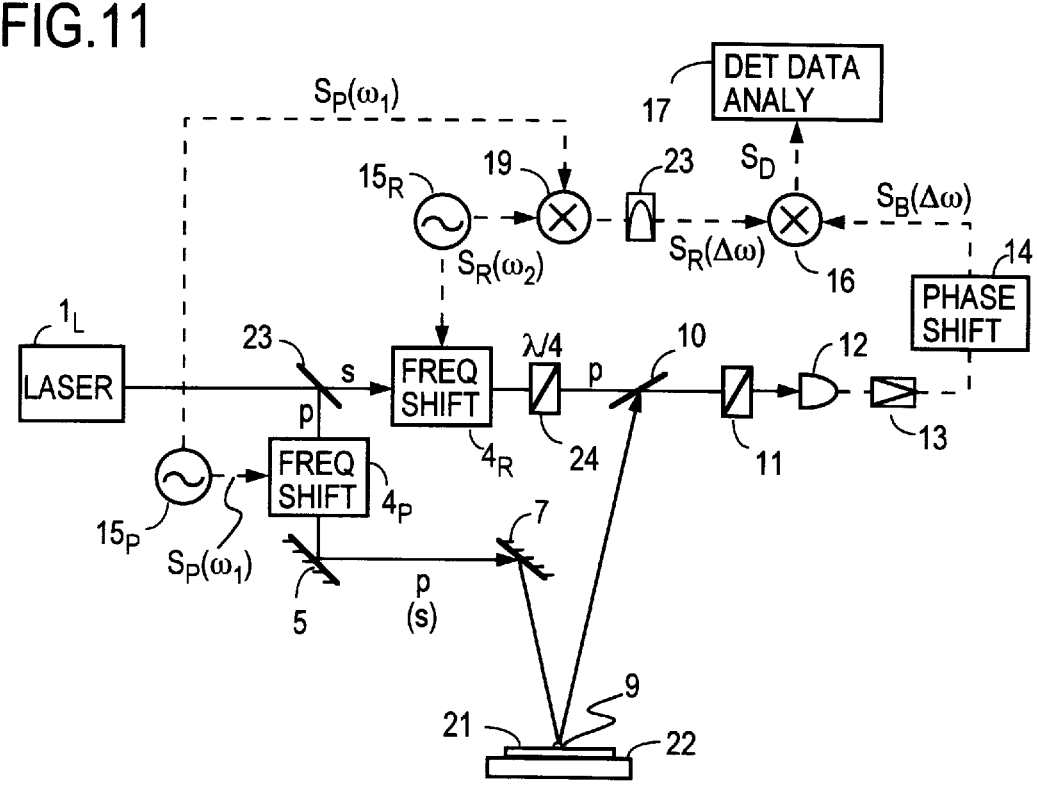
FIG. 11 is a schematic view of a further modification applied to FIG. 7 or 9.

FIG. 11 illustrates the application of the technique described in connection with FIG. 10 to the embodiment shown in FIG. 7. In this modification, the beam splitter 3 having no dependency upon polarization which is shown in FIG. 7 is replaced by a polarization beam splitter 23, the polarization filter 6 is omitted and a quarter-wave plate 24 is disposed in the optical path of the reference light between the polarization beam splitter 23 and a synthesizing beam splitter 10. In other respects, the arrangement is similar to that of the embodiment shown in FIG. 7, and will not be described. It will be readily apparent that the embodiments shown in FIGS. 2 and 4 can be similarly modified by replacing the beam splitter 3 having no dependency upon polarization by the polarization separating prism 23 and by disposing the quarter-wave plate 24 in the optical path of the reference light.

In each of the embodiments shown in FIGS. 2, 4 and 6 to 11, it has been described that the reference signal $S_R(\Delta\omega)$ and the beat signal $S_B(\Delta\omega)$ are mixed, for example, in the parameter extractor 16, which derives a difference signal to be used as a detection signal $S_D$. This takes advantage of the fact that the p-polarization component in the probing light is converted, by the influence of the birefringent foreign matter, into s-polarization, for example, for part or all of the power thereof, whereby the amplitude of the beat signal $S_B(\Delta\omega)$ is reduced or becomes substantially equal to zero. Such a change in the amplitude is detected by obtaining a difference signal between the beat signal $S_B(\Delta\omega)$ and the reference signal $S_R(\Delta\omega)$ by an electrical heterodyne detection. However, a microscopic foreign matter on a semiconductor substrate may influence upon probing light in a manner to change the polarization, to change the amplitude or to change the phase depending on the variety, size and the orientation of the material, and a resulting change may be a combination of these different influences. Accordingly, the detected beat signal may have its phase, amplitude or both influenced depending on the variety, size and the orientation of the foreign matter.

Figure 12:
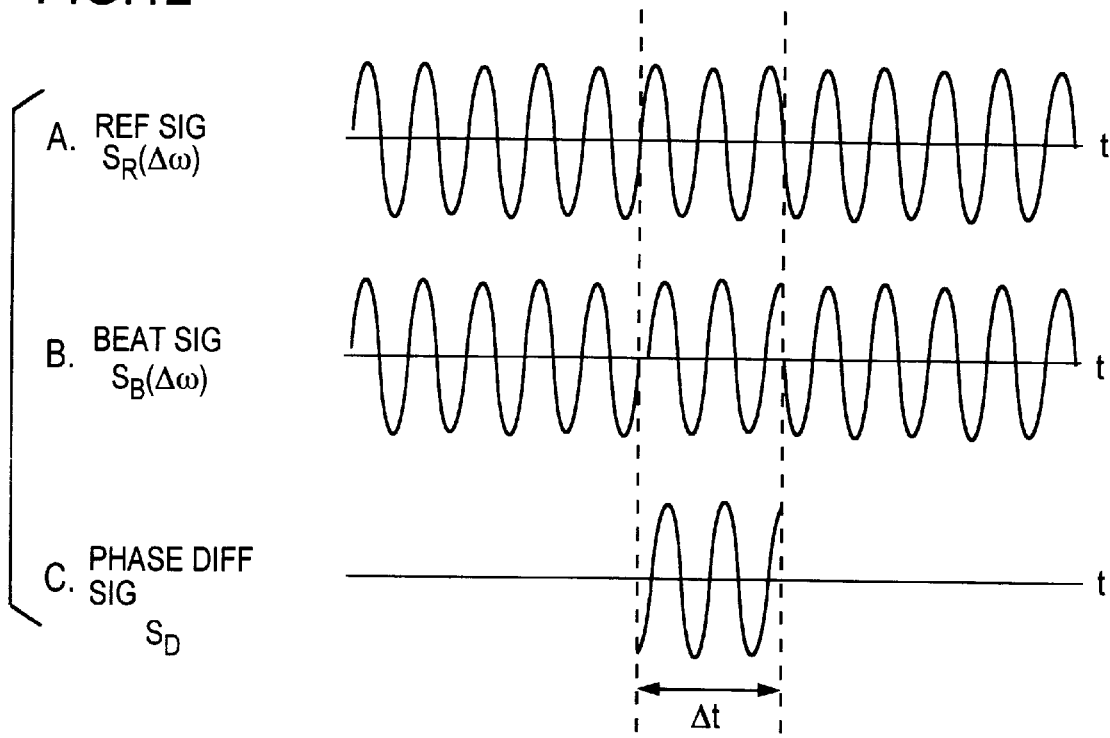
FIG. 12 graphically illustrates waveforms of a beat signal and a difference signal relative to the waveform of a reference signal when the phase of probing light changes due to the presence of a microscopic foreign matter.
Figure 13:
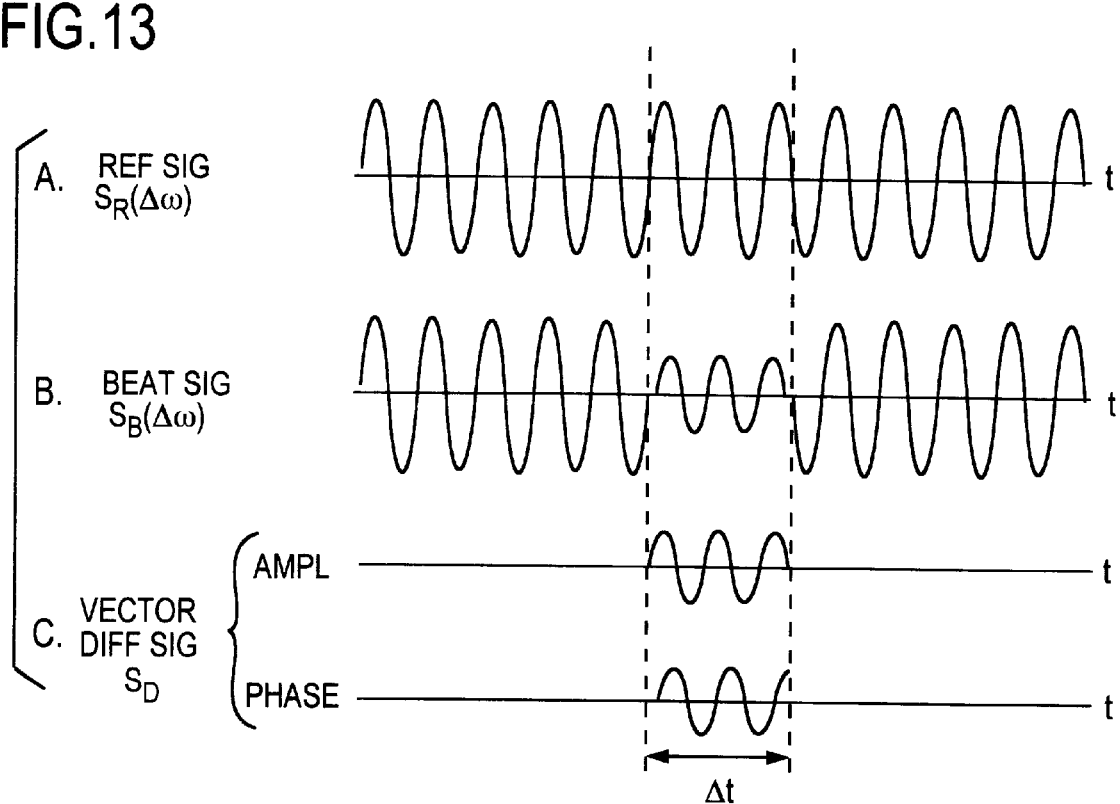
FIG. 13 graphically illustrates waveforms of a beat signal and a difference signal relative to the waveform of a reference signal when both the phase and the amplitude of probing light change due to the presence of a microscopic foreign matter.

Referring to FIG. 12, a waveform B is an exemplary waveform of a beat signal $S_B(\Delta\omega)$ which is detected over a reference signal $S_R(\Delta\omega)$ which is indicated by a waveform A, illustrating that there occurs a change in the phase of the beat signal $S_B(\Delta\omega)$ in a section of a foreign matter or a time interval $\Delta t$. Referring to FIG. 13, a waveform B shows another exemplary waveform of a beat signal $S_B(\Delta\omega)$ which is detected over a reference signal $S_R(\Delta\omega)$ which is indicated by a waveform A, illustrating that both the amplitude and the phase (and hence signal vector) of a beat signal change during a section of a foreign matter or a time interval $\Delta t$. Accordingly, by analyzing the phase and the amplitude of the beat signal, more detailed information concerning the foreign matter can be obtained. Specifically, the phase, the amplitude or the both of the beat signal can be utilized as parameters representative of the nature of the foreign matter. The described embodiments illustrate the detection of a change in the amplitude of the beat signal by the parameter extractor 16, as one of such parameters. To detect a change in the phase of the beat signal, a phase detector may be provided in place of the parameter extractor in each of the embodiments mentioned above. In this manner, a waveform detecting a change in the phase which the probing light has undergone during a time interval $\Delta t$ corresponding to a section for a foreign matter can be obtained, as indicated by a waveform C shown in FIG. 12, for example. Where it is desired to detect a vector change of the beat signal, a vector detector 16 may be provided in place of the parameter extractor 16 shown in the described embodiments, a change in the phase and the amplitude which the probing light undergoes under the influence of the foreign matter may be detected as a change in the phase and the amplitude of the beat signal $S_B(\Delta\omega)$ shown by the waveform B of FIG. 13, thus deriving amplitude information and phase information in a manner illustrated by a waveform C shown in FIG. 13.

In the described embodiments, the optical path has been assumed as comprising a spatial optical path, but it should be understood that except for an optical path on which the probing light irradiates a specimen to be inspected and an optical path on which reflected light from the specimen is received, any optical path or paths between the adjacent optical elements may comprise optical fibers.

The detection data analyzer 17 employs an electronic computer to perform a signal processing of a signal representing a parameter and extracted from the beat signal $S_B(\Delta\omega)$ and the reference signal $S_R(\Delta\omega)$ in a manner described below to calculate the shape and the size of a microscopic foreign matter. Specifically, the surface of a semiconductor substrate on which a circuit is formed is provided with uneven patterns which are formed by wiring patterns and electronic elements disposed to define the circuit, and the polarization and/or phase of the probing light is influenced to change by the edges of the unevenness, and thus the apparatus of the invention inevitably detect these patterns. It will be appreciated that these circuit patterns stand in the way to the detection of a microscopic foreign matter. To avoid the influence of these circuit patterns, the detection data analyzer 17 used in each of the embodiments shown in FIGS. 2, 4 and 6 to 11 is constructed in a manner illustrated in FIG. 14, for example, and a measurement takes place according to a procedure of measurement shown in FIG. 15.

Figure 14:
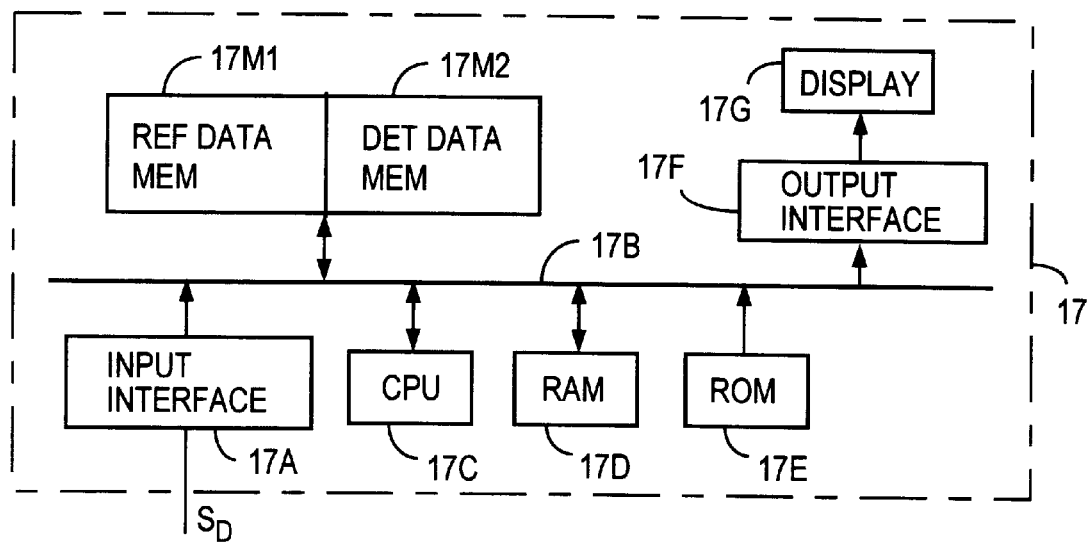
FIG. 14 is a block diagram of a detection data analyzer.
Figure 15:
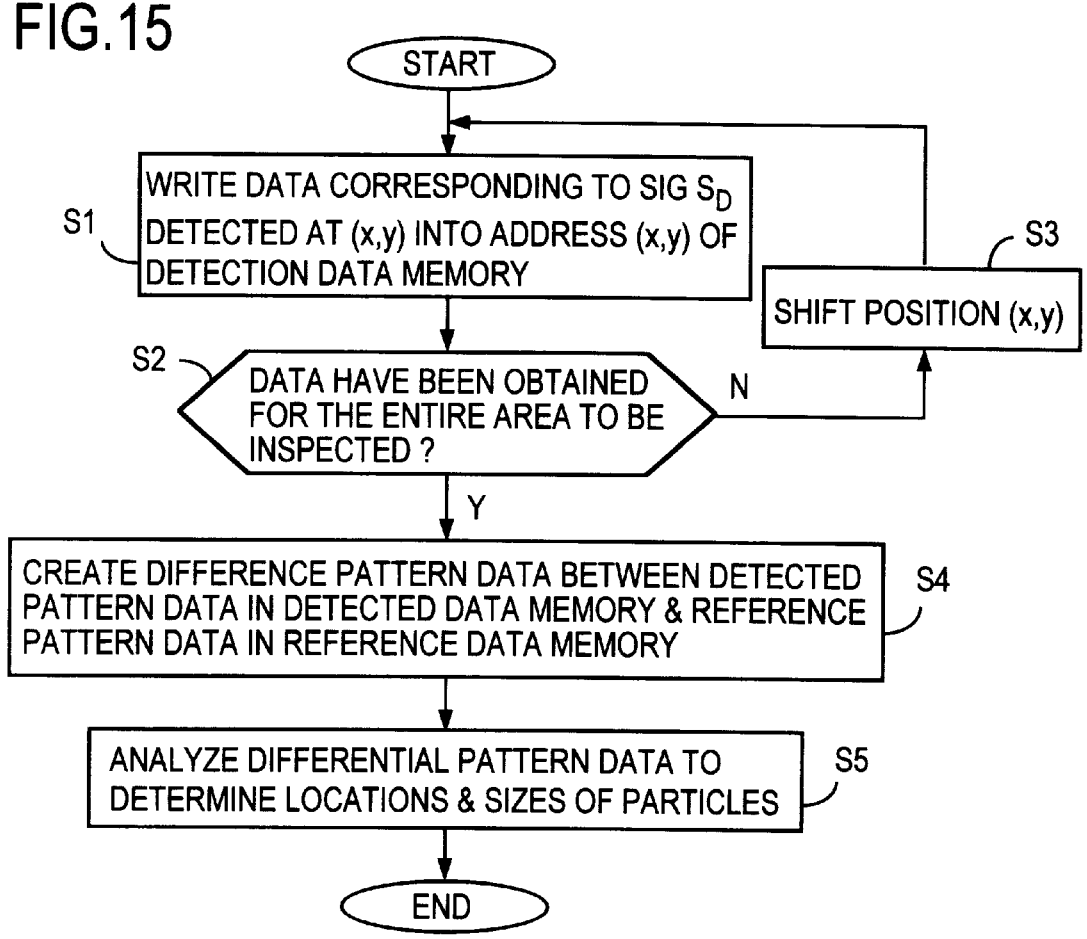
FIG. 15 is a flow chart showing a procedure of detecting the presence of a microscopic foreign matter and processing therefor.

Referring to FIG. 14, the detection data analyzer 17 comprises an input interface 17 which detects an envelope of the parameter detection signal $S_D$ from the parameter extractor 16 and stores it after its A/D conversion, an ROM 17E in which the procedure of measurement used with the apparatus of the invention is stored as a program, an RAM 17D which performs an image data processing operation, a reference data memory 17M1 in which reference pattern data is stored, a detection data memory 17M2 which stores detected pattern data, and a CPU 17C which controls data and executes a processing operation in accordance with the procedure of measurement, these components being interconnected together through a bus 17A. If required, image data for a foreign matter detected may be fed through an output interface 17F to a display 17G for displaying it.

A pattern data which is obtained using the apparatus of the invention while scanning a semiconductor substrate on which no foreign matter is present is stored as reference pattern data in the reference pattern data memory 17 M1. The reference pattern data is prepared by the same procedure as used for inspecting a semiconductor substrate to be inspected, as will be detailed below. Before starting the measurement, a speed of movement and an extent of the movement of the stage 22 are preset.

At step S1, data which is based on the detection signal $S_D$ at coordinates (x,y) of the beam spot is written into the detection data memory 17 M2 at a corresponding address.

At step S2, a determination is made to see if the (x,y) scan has been finished over the entire preset extent.

If the scan is not finished, the location (x,y) of the stage 22 is moved at step S3, and then the operation returns to step S1, subsequently repeating step S1.

If the scan has been finished over the entire preset extent, then at step S4, a difference pattern data between the reference pattern data stored in the reference data memory 17 M1 and the detected pattern data stored in the detected data memory 17 M2 is formed in the RAM 17D.

Subsequently, at step S5, the difference pattern data is analyzed to identify the location and the size of a foreign matter, whereupon the measurement is completed.

In this manner, by previously storing a result of inspection of a semiconductor substrate on which no microscopic foreign matter is present as reference pattern data in the reference data memory, and forming a difference between a detection pattern, representing a result of actual inspection of semiconductor substrate being inspected, and the reference pattern, the reference pattern which is inherent to the semiconductor substrate being inspected itself and representing a background can be cancelled out, allowing only a foreign matter or defect to be extracted. Where a single whole perfect specimen which is free from the microscopic foreign matter cannot be provided, a plurality of specimen may be provided and regions of these specimen where a microscopic foreign matter is absent can be combined together to synthesize a single whole perfect specimen.

Figure 1:
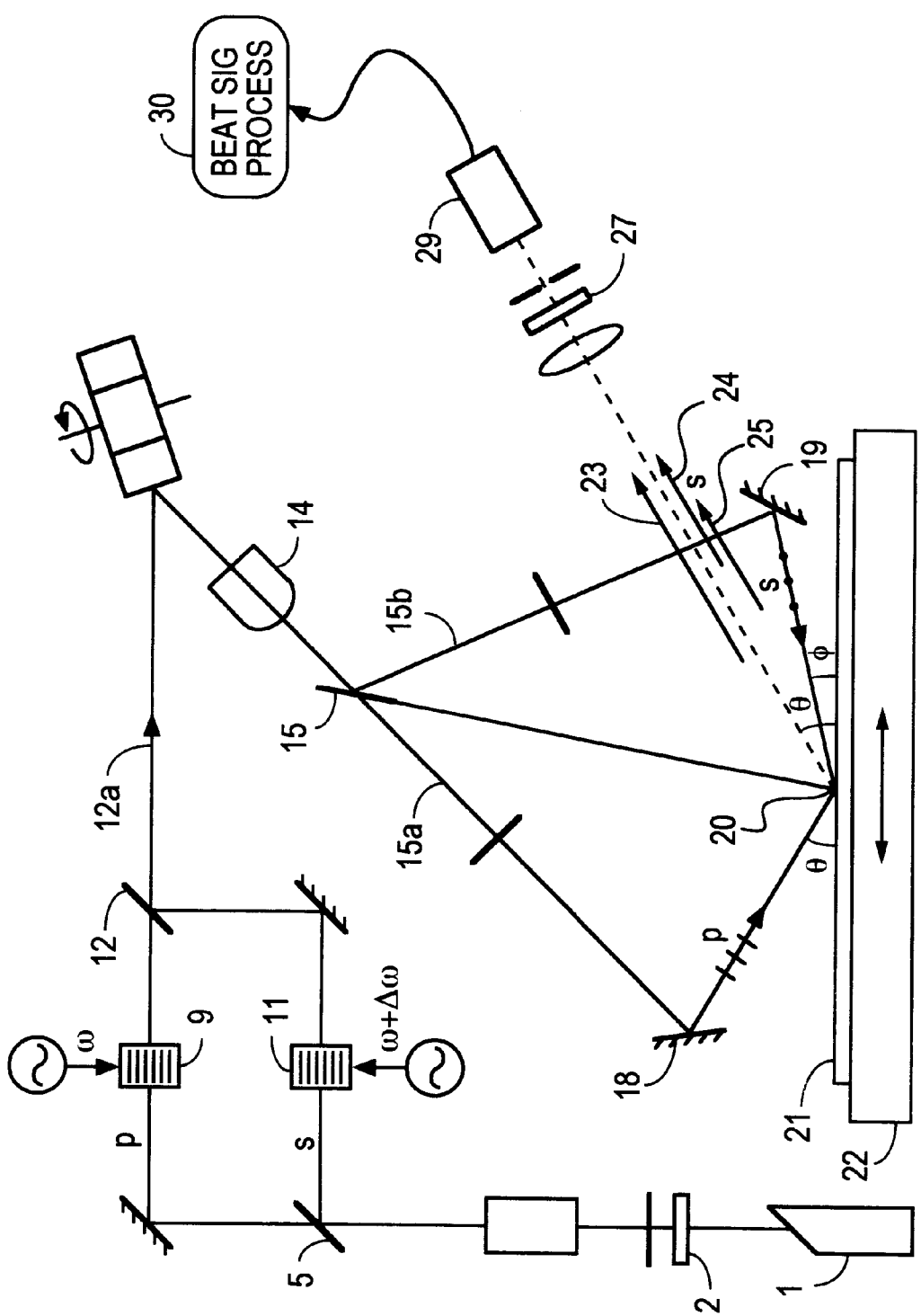
FIG. 1 is a schematic view of a conventional apparatus for inspecting foreign matter by a heterodyne detection using polarized light beams.
Figure 16:
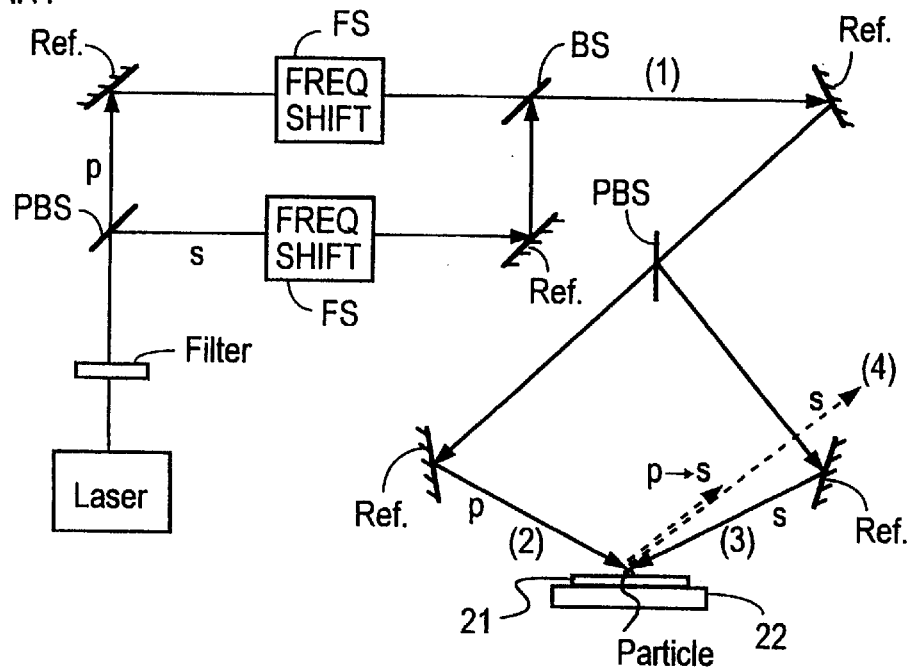
FIG. 16 is a schematic view which is redrawn from FIG. 1 for comparison of the efficiency of light utilization.
Figure 17:
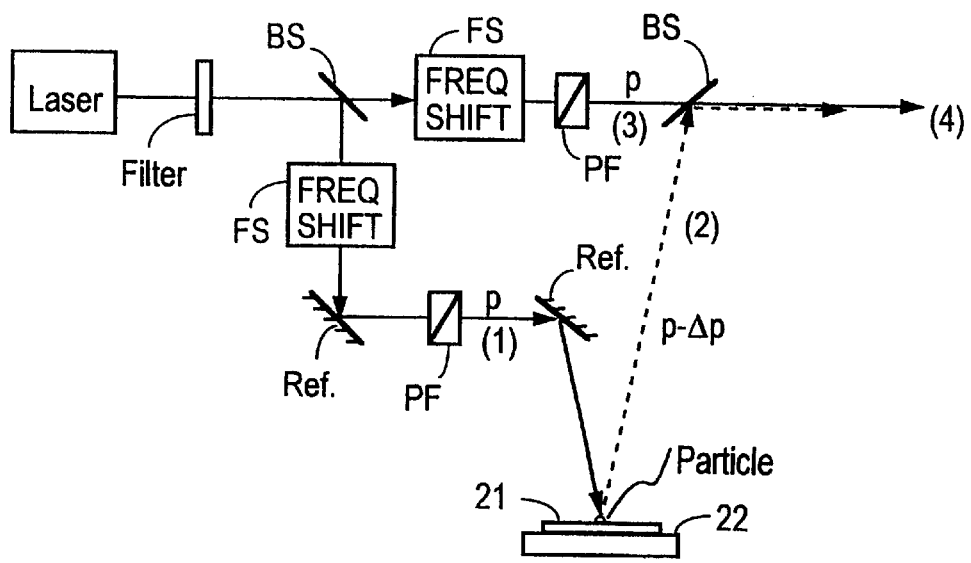
FIG. 17 is a schematic view redrawn from FIG. 4 for comparison of the efficiency of light utilization.

The prior art arrangement shown in FIG. 1 and the arrangement according to the invention as shown in FIG. 7 are partially simplified and reproduced in FIGS. 16 and 17, respectively, and a comparison between the dual polarization probing of the prior art and the dual polarization probing according to the invention in respect of light utilization efficiency is indicated in a chart of FIG. 18. In the chart of FIG. 18, the luminous energy of the probing light and the reference light at the locations (1), (2), (3) and (4) in the optical paths shown in FIGS. 16 and 17 are given as relative values when the luminous energy from the laser source is equal to 1. In FIG. 17, the splitting ratio by the beam splitter BS is chosen such that the power ratio between the probing light and the reference light is substantially equal to 1:1 at location (4) or upon incidence on the photoelectric transducer under the conditions mentioned below. In both FIGS. 16 and 17, the power at each location is calculated under the common conditions given below:

Filter: transmittance 100%

PBS (Polarization Beam Splitter); transmittance 70%, proportion of luminous energy of p-wave: s-wave=1:1

BS (Beam Splitter): transmittance 80%, power ratio at 1:99, combining at ratio of 1:1

FS (Frequency Shifter): transmittance 70%

PF (Polarization Filter): transmittance 70%, a proportion of luminous energy of p-wave: s-wave=1:1

Particle p→s, s→p conversion rate: 10%, reflectance 5%

Laser output luminous energy: 1.000

It will be understood from the result given in the chart that the single polarization probing according to the invention provides more luminous energy on the light receiving surface of the photoelectric transducer and provides a higher sensitivity as compared with the dual polarization probing. The ratio of luminous energy between the probing light and the reference light is equal to 1:10 for the dual polarization probing, and will be approximately equal to 1:1 for the single polarization probing, thus improving the S/N ratio.

EFFECT OF THE INVENTION

As described, in accordance with the invention, the optical probing takes place by using either one of p- or s-polarization, and the light beam which results from the optical probing is optically heterodyned to provide a beat signal $S_B(\Delta\omega)$ which is electrically processed to detect the presence of the foreign matter. In this manner, an optical system which carries out the optical probing can be constructed in a simple manner while increasing the intensity of a signal, which represent a result of inspection for a foreign matter.

As compared with an optical system in which the optical probing takes place by using dual polarization components, the optical system can be simplified. In this manner, where the apparatus of the invention is used in combination with other analytical instrument, a greater freedom of disposing components of the instruments is afforded.

In an apparatus for inspecting for foreign matter which uses dual polarization components for the optical probing, it will be seen that the light beam is separated into mutually orthogonal linear polarizations or p- and s-wave, one of which is used as the probing light while the other is used as the reference light. Accordingly, a proportion of luminous energy between the both is necessarily at a ratio of 1:1. As mentioned above, the proportion at which the probing light is influenced by a foreign matter or a defect present on the surface of a surface to be inspected to be changed into scattered light is as low as several percents, and thus the luminous energy for the detection signal is low, and the signal intensity cannot be increased. By contrast, in accordance with the invention, where the probing light irradiates a specimen to be inspected and is then synthesized with the reference light again to be optically heterodyned on the light receiving surface of the photoelectric transducer, the proportion of luminous energy between the branches which is provided by the beam splitter can be chosen so that the luminous energy of the both on the light receiving surface be substantially equal to each other, thus allowing a beat signal of a higher S/N ratio to be obtained.

In addition, by choosing a beat frequency in a region slightly higher than the corner frequency, using a narrow bandwidth amplifier 13 to amplify a beat signal $S_B(\Delta\omega)$ which is obtained by converting a light signal obtained by performing an optical probing into an electrical signal, and choosing the center frequency of the passband to be equal to the beat frequency to limit the passband of an output from the photoelectric transducer 12, 1/f noises form the photoelectric transducer 12 can be eliminated.

Additionally, by using a polygon mirror for a reflecting mirror which is used in irradiating a specimen to be inspected so that the irradiation sweeps a certain area of the specimen or by providing a stage 22 on which the specimen 21 is placed to be moveable in a plane parallel to the surface thereof, the irradiation of the probing light may be performed in a manner to sweep the foreign matter, thus allowing a size and a shape of the foreign matter to be determined. In addition, the parameter extractor 16 allows a difference signal for a desired parameter which corresponds to the nature of the foreign matter to be obtained from the beat signal and the reference signal.

Finally, by providing a reference pattern memory which previously stores a reference pattern representing a result of inspection of a specimen on which no foreign matter is present, and a data memory which stores a result of actual inspection of a specimen being inspected in the detection data analyzer 17, the presence of a foreign matter is extracted as a difference between the stored contents of the both memories while canceling out common data, thus allowing the inspection for any foreign matter to be achieved rapidly and accurately.

What is claimed is:

1. A method of inspecting a foreign matter on a specimen to be inspected comprising the steps of:
   (a) producing a probing light beam having either a p-wave or an s-wave linear polarization and a reference light beam which includes at least the same polarization component as the linear polarization of the probing light beam from a coherent light beam emitted from a light source;
   (b) generating a reference signal having a predetermined offset frequency;
   (c) providing a frequency offset of the predetermined offset frequency between the reference light beam and the probing light beam;
   (d) irradiating the probing light beam which has the frequency offset relative to the reference light beam onto the specimen to be inspected and providing a relative movement between an irradiating spot of the probing light beam and the specimen;
   (e) synthesizing the probing light beam reflected from the specimen and the reference light beam with each other to impinge on a polarization separating filter through which only the same polarization component in the reference light beam as that of the probing light beam as well as the-reflected probing light beam are allowed to pass;
   (f) impinging output light components to the synthesized probing light beam and the reference light beam derived from said filter on a photoelectric transducer to cause an optical heterodyne detection of the polarized components of said one polarization of both the probing light beam and reference light beam to thereby detect the frequency offset to thereby obtain a beat signal having the offset frequency;
   (g) adjusting amplitude and phase of the beat signal;
   (h) extracting various parameters representing natures of a foreign matter present on the specimen from the beat signal thus adjusted and the reference signal; and
   (i) analyzing the extracted parameters to derive information concerning the foreign matter.

2. The method according to claim 1 in which
the step (c) comprises the step of applying a frequency shift to one of the probing light beam and the reference light beam with respect to the other by a modulation signal of the offset frequency to produce the frequency offset therebetween, whereby the beat signal obtains a frequency which is equal to the frequency offset.

3. The method according to claim 2 in which
a modulation signal used in the step (c) represents the reference signal, and in which
   the step (h) comprises the step of obtaining a detection signal representing the parameter from an amplitude difference between the reference signal and the beat signal, and
   the step (i) comprises the step of deriving information concerning to the foreign matter from the detection signal.

4. The method according to claim 2 in which
a modulation signal used in the step (c) comprises the reference signal, and in which
   the step (h) comprises the step of obtaining a detection signal representing the parameter from a phase difference between the reference signal and the beat signal, and
   the step (j) comprises the step of deriving information concerning to the foreign matter from the detection signal.

5. The method according to claim 2 in which
a modulation signal used in the step (c) comprises the reference signal, and in which
   the step (h) comprises the step of obtaining a detection signal representing the parameter from a vector difference between the reference signal and the beat signal, and
   the step (i) comprises the step of deriving information concerning to the foreign matter from the detection signal.

6. The method according to claim 1 in which the step (c) comprises the steps of modulating the probing light beam and the reference light beam with a first modulation signal of a first frequency and a second modulation signal of a second frequency which is different from the first frequency with the predetermined offset frequency, respectively, thereby providing the beat signal having a frequency which is equal to a difference between the first and the second frequency, the first and second modulation signals of the first and the second frequency being mixed in mixer means to provide a signal having the offset frequency therebetween as the reference signal.

7. The method according to claim 6 in which
the step (h) comprises the step of obtaining a detection signal representing the parameter from an amplitude difference between the reference signal and the beat signal.

8. The method according to claim 6 in which
the step (h) comprises the step of obtaining a detection signal representing the parameter from a phase difference between the reference signal and the beat signal.

9. The method according to claim 6 in which
the step (h) comprises the step of obtaining a detection signal representing the parameter from a vector difference between the reference signal and the beat signal.

10. The method according to claim 1, in which the step (a) comprises the steps of:
passing the coherent light beam from the light source which contain p- and s-polarization through a beam splitter having no dependency upon polarization to be divided into two branched beams; and
extraction from one of the two branched beams one of the p- and the s-polarization by using a polarization filter to provide the probing light beam while the other beam of the two branched beams is used as the reference light beam.

11. The method according to claim 1, in which
the step (a) comprises the step of passing a light beam of a linear polarization derived from the light source through a beam splitter having no dependency upon polarization to be divided into two branched light beams, one of which is used as the probing light beam while the other beam is used as the reference light beam.

12. (The method according to claim 1, in which
the step (a) comprises the steps of passing a laser light beam from the light source which contains both p- and s-polarizations through a polarization beam splitter to be divided into two branched light beams one of which is a p-polarization beam and the other one of which is an s-polarization beam, one of which is used as the probing light beam while the other is passed through a quarter-wave plate to be converted into the same polarization as the polarization of said probing light beam to be used as the reference light beam.

13. The method according to one of claim 1, 2 or 6 in which
the step (e) comprises the steps of synthesizing the probing light beam reflected from the specimen and the reference light beam in a synthesizing beam splitter to provide a synthesized beam which then impinges on the photoelectric transducer means.

14. The method according to claim 13 in which
the synthesized beam is passed through a polarization filter having the same polarization axis as the probing light beam before it impinges on the photoelectric transducer means.

15. The method according to one of claim 3, 4, 5, 7, 8 or 9, in which
the step (g) of adjusting the amplitude and phase of the beat signal is so effected that the detecting signal becomes close to zero in a region on the surface of the specimen which is free from a foreign matter before starting the inspection.

16. The method according to claim 15 in which
the amplitude of the beat signal is adjusted by a narrow bandwidth amplifier means which amplifies an output from the photoelectric transducer means, the amplifier means having a center frequency which is chosen to be higher than the corner frequency of the photoelectric transducer means, the frequency of the modulation signal being chosen so that the frequency of the beat signal is equal to the center frequency of the narrow bandwidth amplifier means.

17. The method according to one of the claim 3, 4, 5, 7, 8 or 9, in which
the step (d) includes the step of scanning a region to be inspected on the surface of the specimen with the irradiating spot, and
in which the step (i) comprises the steps of:
storing pattern data which is based on the detection signal obtained from a specimen which is similar to a specimen to be inspected, but which is free from any foreign matter as reference pattern data in memory means, and
comparing detected pattern data which is based on the detection signal obtained from the actual inspection of the specimen to the reference pattern data to provide difference pattern data from which the presence of a foreign matter is detected.

18. The method according to claim 10, in which
the beam splitter used in the step (a) is so determined that a proportion of luminous energy between the probing light beam and the reference light beam upon incidence upon the photoelectric transducer is substantially equal to 1:1.

19. An apparatus for inspecting foreign matter by a heterodyned detection of polarizations, comprising:
(a) a light source emitting a coherent light beam;
(b) a beam splitter producing a probing light beam having a linear polarization and a reference light beam which includes at least the same polarization component as the linear polarization of the probing light beam from the light beam emitted from the light source;
(c) frequency modulation means for effecting frequency modulation on at least one of the reference light beam and the probing light beam to provide a frequency offset therebetween;
(d) a reference signal generator producing a reference signal having the offset frequency;
(e) scan means for irradiating the probing light beam a specimen to be inspected and providing a relative movement between an irradiating spot of the probing light beam and the specimen;
(f) means for synthesizing the probing light beam reflected from the specimen and the reference light beam into a synthesized beam which then impinges on the photoelectric transducer means;
(g) polarization filter means for allowing the same polarization component as that of the probing light beam on the synthesized beam to pass therethrough;
(h) photoelectric transducer means on which output of the polarization filter means is light beam reflected from the specimen and the reference light beam which is modulated relative to the probing light beam impinged to be optically heterodyned to provide a beat signal which represents the frequency offset;

(i) means for adjusting phase and amplitude of the beat signal from the photoelectric transducer;

(j) parameter extracting means for extracting parameters representing natures of a foreign matter present on the specimen from the beat signal adjusted by the means for adjusting and the reference signal; and (k) means for analyzing the extracted parameters to derive information concerning to the foreign matter.

20. The apparatus according to claim 19 in which the frequency modulation means comprises an oscillator generating a modulation signal having a frequency which is equal to the frequency offset, and frequency shift means disposed in the optical path of one of the probing light beam and the reference light beam and driven in accordance with the modulation signal to cause the frequency of either one of the probing light beam and the reference light beam to be shifted relative to the other, thereby allowing the beat signal having a frequency which is equal to the difference frequency to be produced by the photoelectric transducer means.

21. The apparatus according to claim 20 in which the parameter extracting means comprises mixer means which receives the modulation signal as a reference signal and the beat signal to derive a signal representing a difference in the amplitude therebetween as a detection signal representing the parameter, and the means for analyzing the extracted parameters derives information concerning to the foreign matter from the detection signal.

22. The apparatus according to claim 20 in which the parameter extracting means comprises phase difference detecting means which receive the modulation signal as a reference signal and the beat signal to derive a signal representing a difference in the phase therebetween in the form of a detection signal representing the parameter, and the means for analyzing the extracted parameters derives information concerning to the foreign matter from the detection signal.

23. The apparatus according to claim 20 in which the parameter extracting means comprises vector difference detecting means which receive the modulation signal as a reference signal and the beat signal to derive a signal representing a vector difference therebetween in the form of a detection signal representing the parameter, and the means for analyzing the extracted parameters derives information concerning a foreign matter from the detection signal.

24. The apparatus according to claim 19 in which the frequency modulation means comprises:

first and second oscillators producing a modulation signal of a first frequency and a modulation signal of the second frequency which is different from the first frequency, first and the second frequency shift means disposed in the optical path of the probing light beam and in the optical path of the reference light beam, respectively, and driven in accordance with the modulation signals of the first and the second frequency, respectively, for shifting the frequencies of the probing light beam and the reference light beam by the first and the second frequency, thereby allowing the beat signal having a frequency which is equal to a difference between the first and the second frequency to be produced by the photoelectric transducer means, and first mixer means for mixing the modulation signals of the first and the second frequencies to provide a signal having an offset frequency therebetween as the reference signal.

25. The apparatus according to claim 24 in which the parameter extractor means comprises second mixer means which receives the reference signal and the beat signal to produce a signal representing a difference in the amplitude therebetween in the form of a detection signal representing the parameter, and the detection data analyzing means derives information concerning to the foreign matter on the basis of the detection signal.

26. The apparatus according to claim 24 in which the parameter extractor means comprises phase difference detecting means which receives the reference and the beat signal to produce a signal representing a phase difference therebetween in the form of a detection signal representing the parameter, and the detection data analyzing means derives information concerning to the foreign matter on the basis of the detection signal.

27. The apparatus according to claim 24 in which the parameter extractor means comprises, vector difference phase detecting means which receives the reference and the beat signal to produce a signal representing a vector difference therebetween in the form of a detection signal representing the parameter, and the detection data analyzing means derives information concerning to the foreign matter on the basis of the detection signal.

28. The apparatus according to claim 19 in which the light source means emits a coherent light beam having p-polarization and s-polarization, and the beam forming means comprises:

a beam splitter having no dependency upon polarization which divides the light beam from the light source means which includes the p-polarization and the s-polarization into two branched beams, and a polarization filter which selects either one of the p- and the s-polarization from one of the branched beams for use as the probing light beam, the other one of the branched beams being used as the reference light beam.

29. The apparatus according to claim 19 in which the light source means emits a coherent light beam having a linear polarization, and the beam splitter means comprises non-polarization-dependent beam splitter which divides the light beam having the linear polarization from the light source means into a pair of beams without dependency upon polarization, one of the beams being used as probing light beam while the other beam is used as reference light beam.

30. The apparatus according to claim 19 in which the light source means emits a coherent laser light beam having p-polarization and s-polarization, and the beam splitter means comprises:

a polarization beam splitter dividing the laser light beam from the light source means which contains p- and s-polarizations into a p-polarization beam and an s-polarization beam, one of the p- and s-polarization beams being delivered as the probing light beam, and a quarter-wave plate rotating the polarization axis of the other one of the p- and s-polarization beams through 90° to deliver it as the reference light beam having the same polarization axis as that of said one of the p- and s-polarization beams.

31. The apparatus according to one of claims 19, 20 and 24, in which the means for synthesizing comprises a synthesizing beam splitter synthesizing the probing light beam reflected from the specimen and the reference light beam into a synthesized beam which then impinges on the photoelectric transducer means.

32. An apparatus according to claim 31, in which said polarization filter means comprises a polarization filter having the same polarization axis as the probing light and allowing the same component in the synthesized beam as its polarization axis to pass therethrough to impinge on the photoelectric transducer means.

33. The apparatus according to one of claims 21, 22, 23, 25, 26 and 27, in which:

the means for adjusting phase and amplitude of the beat signal comprises amplifier means and phase shift means disposed on the output side of the photoelectric transducer means for adjusting the phase and the amplitude of the beat signal so that the detection signal becomes equal to zero for a region on the surface of the specimen which is free from a foreign matter, the adjustment taking place before starting the inspection.

34. The apparatus according to claim 33 in which the amplifier means comprises narrow bandwidth amplifier means having a center frequency which is chosen to be higher than the corner frequency of the photoelectric transducer means, the frequency of the modulation signal being chosen so that the frequency of the beat signal is equal to the center frequency of the narrow bandwidth amplifier means.

35. The apparatus according to one of claims 21, 22, 23, 25, 26 and 27 in which:

the scan means includes means for scanning a region to be inspected on the surface of the specimen with the irradiating spot, and means for analyzing the extracted parameters comprises
memory means for storing pattern data based on the detection signal which is obtained previously by inspecting a specimen similar to the specimen to be inspected, but which is free from a foreign matter as reference pattern data, and means for forming a difference pattern data between detected pattern data based on the detection signal which is obtained from an actual inspection of the specimen and the reference pattern data and for detecting the presence of a foreign matter in accordance with the difference pattern data.

36. The method according to claim 2, in which the step (a) comprises the steps of passing the light beam from the light source means which contain p- and s-polarization through a beam splitter having no dependency upon polarization to be divided into two branched beams, and extracting from one of the two branched beams one of the p- and the s-polarization by using a polarization filter to provide the probing light beam while the other beam is used as the reference light beam.

37. The method according to claim 6, in which the step (a) comprises the steps of passing the light beam from the light source means which contain p- and s-polarization through a beam splitter having no dependency upon polarization to be divided into two branched beams, and extracting from one of the two branched beams one of the p- and the s-polarization by using a polarization filter to provide the probing light beam while the other beam is used as the reference light beam.

38. The method according to claim 2, in which the step (a) comprises the step of passing a light beam of a linear polarization derived from the light source means through a beam splitter having no dependency upon polarization to be divided into two branched light beams, one of which is used as the probing light beam while the other beam is used as the reference light beam.

39. The method according to claim 6, in which the step (a) comprises the step of passing a light beam of a linear polarization derived from the light source means through a beam splitter having no dependency upon polarization to be divided into two branched light beams, one of which is used as the probing light beam while the other beam is used as the reference light beam.

40. The method according to claim 2, in which the step (a) comprises the steps of passing a laser light beam from the light source means which contains both p- and s-polarizations through a polarization beam splitter to be divided into two branched light beams one of which is a p-polarization beam and the other one of which is an s-polarization beam, one of which is used as the probing light beam while the other is passed through a quarter-wave plate to be converted into the same polarization as the polarization of said probing light beam to be used as the reference light beam.

41. The method according to claim 6, in which the step (a) comprises the steps of passing a laser light beam from the light source means which contains both p- and s-polarizations through a polarization beam splitter to be divided into two branched light beams one of which is a p-polarization beam and the other one of which is an s-polarization beam, one of which is used as the probing light beam while the other is passed through a quarter-wave plate to be converted into the same polarization as the polarization of said probing light beam to be used as the reference light beam.

42. The method according to claim 11, in which the beam splitter used in the step (a) is so determined that a proportion of luminous energy between the probing light beam and the reference light beam upon incidence upon the photoelectric transducer is substantially equal to 1:1.

43. The method according to claim 12, in which the beam splitter used in the step (a) is so determined that a proportion of luminous energy between the probing light beam and the reference light beam upon incidence upon the photoelectric transducer is substantially equal to 1:1.

44. The apparatus according to claim 19, in which the beam splitter means is so designed that a proportion between amount of the probing light beam and that of the reference light beam upon incidence upon the photoelectric transducer means becomes equal to 1:1.

45. The apparatus according to claim 28, in which the beam splitter included in the beam splitter means is so designed that a proportion between amount of the probing light beam and that of the reference light beam upon incidence upon the photoelectric transducer means becomes equal to 1:1.

46. The apparatus according to claim 29, in which the beam splitter included in the beam splitter means is so designed that a proportion between amount of the probing light beam and that of the reference light beam upon incidence upon the photoelectric transducer means becomes equal to 1:1.

47. The apparatus according to claim 30, in which the beam splitter included in the beam splitter means is so designed that a proportion between amount of the probing light beam and that of the reference light beam upon incidence upon the photoelectric transducer means becomes equal to 1:1.

* * * * *